(12) United States Patent
Regnier et al.

(10) Patent No.: US 7,867,754 B1
(45) Date of Patent: Jan. 11, 2011

(54) MICROARRAYS FOR ANALYTE DETECTION

(75) Inventors: Fred E. Regnier, West Lafayette, IN (US); Ronald George Reifenberger, West Lafayette, IN (US); Halina Dorota Inerowicz, West Lafayette, IN (US); Stephen Wayne Howell, Albuquerque, NM (US)

(73) Assignee: Purdue Research Foundation, West LaFayette, IN (US)

( * ) Notice: Subject to any disclaimer, the term of this patent is extended or adjusted under 35 U.S.C. 154(b) by 696 days.

(21) Appl. No.: 11/786,757

(22) Filed: Apr. 11, 2007

Related U.S. Application Data

(63) Continuation of application No. 10/633,084, filed on Aug. 1, 2003, now abandoned.

(60) Provisional application No. 60/400,225, filed on Aug. 1, 2002.

(51) Int. Cl.
*C12M 1/34* (2006.01)
*C12M 3/00* (2006.01)

(52) U.S. Cl. .................. 435/287.1; 435/7.1; 435/283.1; 435/287.2; 435/288.7; 436/164; 422/68.1; 422/82.05

(58) Field of Classification Search .................. 435/7.1, 435/283.1, 287.1, 288.7, 287.2; 436/518, 436/164; 422/50, 68.1, 82.05
See application file for complete search history.

(56) References Cited

U.S. PATENT DOCUMENTS

| | | | |
|---|---|---|---|
| 4,353,886 A | 10/1982 | Lutkens et al. | |
| 4,487,839 A | 12/1984 | Kamentsky | |
| 4,647,544 A * | 3/1987 | Nicoli et al. | ................. 436/518 |
| 5,491,097 A | 2/1996 | Ribi et al. | |
| 5,512,490 A | 4/1996 | Walt et al. | |
| 5,736,257 A | 4/1998 | Conrad et al. | |
| 5,837,832 A | 11/1998 | Chee et al. | |
| 6,087,114 A | 7/2000 | Rider | |
| 6,103,479 A | 8/2000 | Taylor | |
| 6,232,072 B1 | 5/2001 | Fisher | |
| 6,238,869 B1 | 5/2001 | Kris et al. | |
| 6,416,642 B1 | 7/2002 | Alajoki et al. | |
| 6,545,758 B1 * | 4/2003 | Sandstrom | .................. 356/317 |
| 6,875,619 B2 * | 4/2005 | Blackburn | ..................... 506/9 |
| 2001/0004526 A1 * | 6/2001 | Everhart et al. | ................. 435/6 |
| 2004/0053322 A1 | 3/2004 | McDevitt et al. | |

OTHER PUBLICATIONS

Berggren et al., "An Immunological Interleukine-6 Capacitive Biosensor Using Perturbation with a Potentiostatic Step," *Biosens. Bioeleciron.*, 1998; 13(10):1061-1068.
Berggern et al., "Review—Capacitive Biosensors," *Electroanalysis*, 2001; 13(3):173-180.
Bernard et al., "Printing Patterns of Proteins," *Langmuir*, 1998: 14(9):2225-2229.

(Continued)

*Primary Examiner*—Melanie J Yu
(74) *Attorney, Agent, or Firm*—Mueting Raasch & Gebhardt, P.A.

(57) ABSTRACT

Method and device for detection of analytes, particularly biohazards. A microarray containing immobilized sensing molecules captures complementary analytes on a redundant patterned substrate. Pattern analysis is performed using a computer algorithm.

25 Claims, 15 Drawing Sheets

OTHER PUBLICATIONS

Bernard et al., "Microcontact Printing of Proteins," *Adv. Mater.*, 2000; 12(14):1067-1070.

"Chemical and Biological Terrorism: Research and Development to Improve Civilian Medical Response," Institute of Medicine and National Research Council, National Academy Press, Washington, D.C., 1999; title page and Appendix B; 4 pgs.

Duchet et al., "Influence of the Deposition Process on the Structure of Grafted Alkylsilane Layers," *Langmuir*, 1997; 13:2271-2278.

Howell et al., "Immunosensing Using Fabricated Protein Microarray," The 7th International Conference on the Commercialization of Micro and Nano System. Sep. 8-12, 2002, Ypsilanti, Michigan USA. 5 pages.

Howell et al., "Patterned Protein Microarrays for Bacterial Detection," *Langmuir*, 2003; 19:436-439.

Inerowicz et al., "Multiprotein Immunoassay Arrays Fabricated by Microcontact Printing," *Langmuir*, 2002: 18:5263-5268.

Inerowicz et al., "Protein Microarray Fabrication for Immunosensing," Abstract to American Chemical Society. Aug. 2002.

Inerowicz et al., "Protein Microarray Fabrication for Immunosensors," American Chemical Society Poster. Aug. 2002.

Jackman et al., "Fabrication of Submicron Features on Curved Surfaces by Microcontact Printing," *Science*, 1995; 269:664-666.

James et al., "Patterned Protein Layers on Solid Substrates by Thin Stamp Microcontact Printing," *Langmuir*, 1998; 14:741-744.

Kane et al., "Patterning Proteins and Cells Using Soft Lithography," *Biomaterials*, 1999; 20:2363-2376.

Kumar et al., "Features of Gold Having Micrometer to Centimeter Dimensions can be Formed Through a Combination of Stamping with an Elastomeric Stamp and an Alkanethiol "Ink" Followed by Chemical Etching," *Appl. Phys. Lett.*, 1993;63(14):2002-2004.

Lahiri et al., "Patterning Ligands on Reactive SAMS by Microcontact Printing," *Langmuir*, 1999; 15:2055-2060.

Lopez et al., "Fabrication and Imaging of Two-Dimensional Patterns of Proteins Adsorbed on Self-Assembled Monolayers by Scanning Electron-Microscopy," *J. Am. Chem. Soc.*, 1993; 115(23):10774-10781.

Mirsky et al., "Capacitive Monitoring of Protein Immobilization and Antigen-antibody Reactions on Monomolecular Alkylthiol Films on Gold Electrodes," *Biosens. Bioelectron.*, 1997; 12(9-10):977-989.

"Molecular Imaging PicoSPM" datasheet [online]. Molecular Imaging, Tempe, AZ, 85282 [retrieved on Apr. 22, 2004]. Retrieved from the Internet:<URL:www.molec.com>; 5 pgs.

Morhard et al., "Immobilzation of Antibodies in Micropatterns for Cell Detection by Optical Diffraction," *Sensors and Actuators B*, 2000; 70:232-242.

Mrksich et al., "Controlling Cell Attachment on Contoured Surfaces with Self-Assembled Monolayers of Alkanethiolates on Gold," *Proc. Natl. Acad. Sci. USA*, 1996; 93:10775-10778.

Ostuni et al., "The Interaction of Proteins and Cells with Self-Assembled Monolayers of Alkanethiolates on Gold and Silver," *Colloids and Surf B: Biointerfaces*, 1999; 15:3-30.

Purdue News Mar. 20, 2003, "*Home Security Experts*" [retrieved on Apr. 13, 2005] Retrieved from the Internet: <URL:http://news.uns.purdue.edu/html3month/030320.T.Homeland.security.html.> 6 pgs.

Reifenberger, "Micro/Nano Sensors for Chemical/Biological Warfare Agents Detection," Purdue University, May 2003, 3 pgs.

Ren et al , "Enrichment of Cysteine-Containing Peptides from Tryptic Digests Using a Quaternary Amine Tag," *Anal. Chem.*, 2004; 76(15):4522-4530.

Rowe et al., "An Array lmmunosensor for Simultaneous Detection of Clinical Analytes," *Anal. Chem.*, 1999; 71:433-439.

Rowe et al., "Array Biosensor for Simultaneous Identification of Bacterial, Viral, and Protein Analytes," *Anal. Chem.*, 1999; 71:3846-3652.

Ruan et al., Immunobiosensor chips for detection of *Escherichia coli* O157:H7 using electrochemical impedance spectroscopy, *Anal. Chem.*, 2002; 74(18):4814-4820.

Singhvi et al., "Engineering Cell Shape and Function," *Science*, 1994; 264:696-698.

Squires, "Concentration and Time Exposure Sensitivity Limitations in Biological Sensors Utilizing Fluorescence and Atomic Force Microscopy," Thesis, Purdue University, Aug. 2003; 58 pgs.

St. John et al., "Diffraction-based Cell Detection Using a Microcontact Printed Antibody Grating," *Anal. Chem.*, 1998; 70(6):1108-1111.

Thompson et al., "Structural characterization of plasmenylcholine photooxidation products," *Photochem Photobiol.*, 2003; 78(4):323-30.

Varma et al., "Spinning-disk self-referencing interferometry of antigen-antibody recognition," Optics Letters, May 2004; 29(9):950-952.

*Webster's Ninth New Collegiate Dictionary*, Merriam-Webster Inc., Springfield, MA, 1990; Title page, Publication page, and pp. 863 and 998.

Zhang et al., "Biological Surface Engineering: a Simple System for Cell Pattern Formation," Biomaterials, 1999; 20:1213-1220.

Rocklin et al., "A microfabricated fluidic device for performing two-dimensional liquid phase separations," *2000 Anal. Chem.* 72:5244-5249.

Ekins and Chu, "Multianalyte microspot immunoassay—microanalytical 'compact disk' of the future," Nov. 1991 *Clin. Chem.* 37(11):1955-1957.

Schweitzer et al., "Multiplexed protein profiling on microarrays by rolling-circle amplification," Apr. 2002 *Nat. Biotechnol.* 20(4):359-365.

Bhatt et al., "An AC electrokinetic technique for collection and concentration or particles and cells on patterned electrodes," 2005 *Langmuir* 21:6603.

Crittenden et al., "Soft lithography based micron-scale electrophoretic patterning of purple membrane," 2005 *J. Micromech. Microeng.* 15:1494-1497.

Dhayal et al., "Detection of *Bacillus subtilis* spores using peptide-functionalized cantilever arrays," 2006 *J. Amer. Chem. Soc.* 128:3716-3721.

Purdue University. Office of Industry Research and Technology Programs *Purdue/Industry Partnerships*. May 2003. vol. 10(1) 12 pages.

Squires, Laura Guirl, "Concentration and time exposure sensitivity limitations in biological sensors utilizing fluorescence and atomic force microscopy," Purdue University Master of Science Thesis. Aug. 2003, pp. 1-60.

* cited by examiner

Microfluidic Network (μFN)

A.

Figure 3b
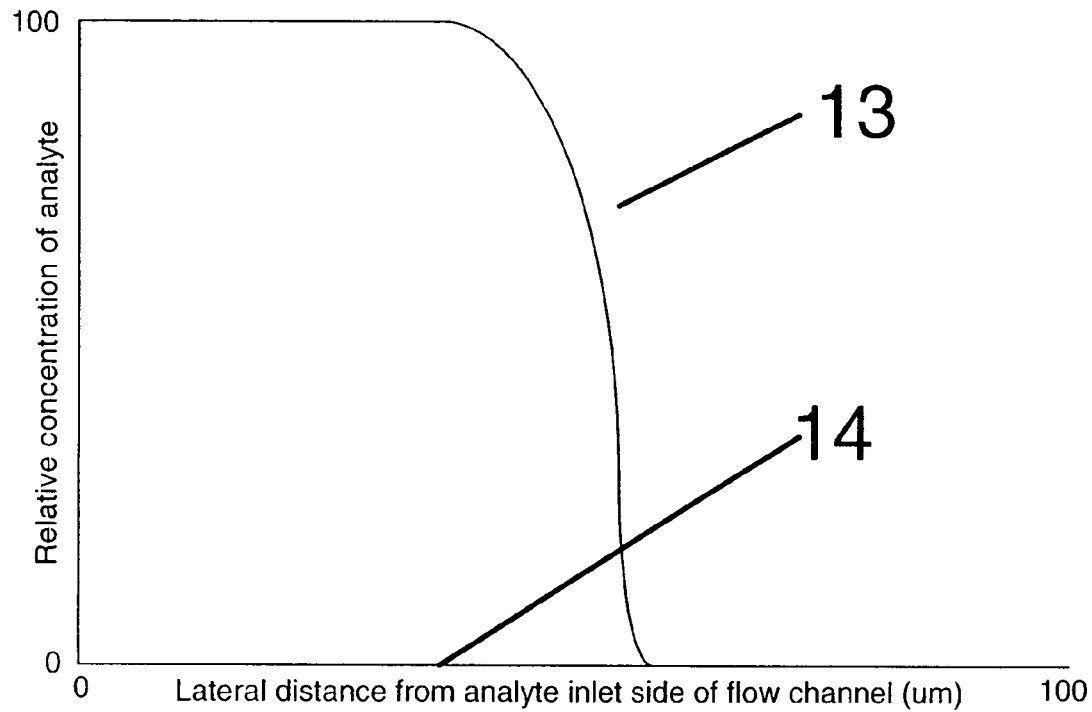
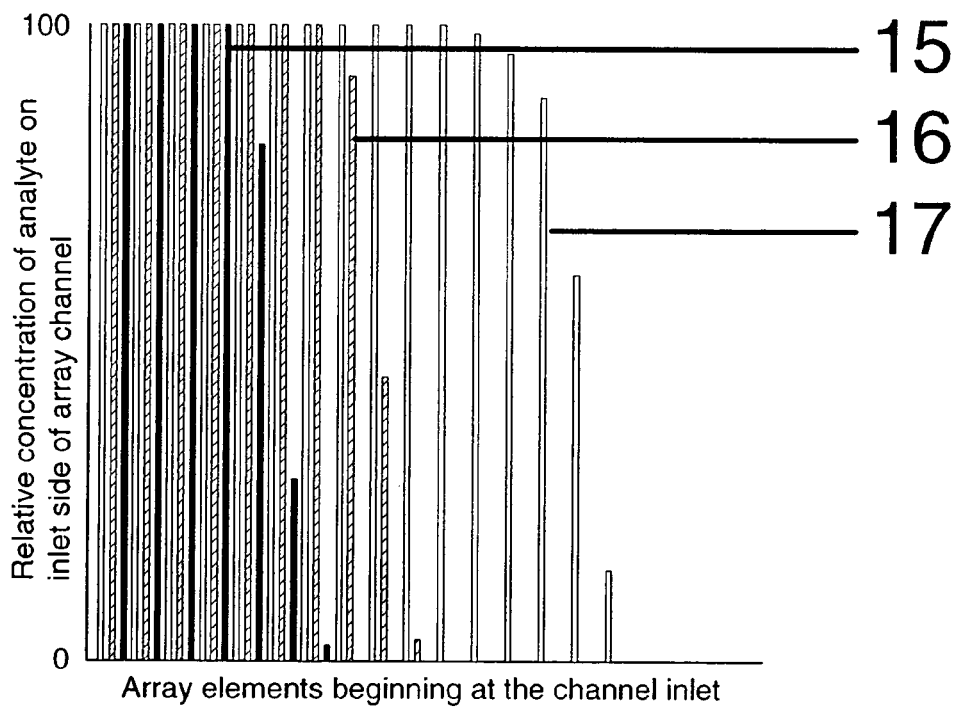
Figure 3c a)

b)

c)

(a)            (b)

MICROARRAYS FOR ANALYTE DETECTION

This application claims the benefit of U.S. Provisional Application Ser. No. 60/400,225, filed 1 Aug. 2002, which is incorporated herein by reference in its entirety.

STATEMENT OF GOVERNMENT RIGHTS

This invention was made with government support under a grant from the United States Navy, Grant No. N00164-00-C-0047. The U.S. Government has certain rights in this invention.

BACKGROUND OF THE INVENTION

Recent events have triggered a strong interest in sensitive detection of viruses and bacteria. Various strategies have been proposed to detect the presence of bacterial contaminants. The traditional technique, in which specimens are collected, cultured and then counted presents problems because of the long time scales usually required. To solve this problem, indirect techniques have been proposed in which the presence of bacteria is rapidly inferred from changes in a transducer output signal. These indirect techniques include electrochemical methods and quartz microbalance detection. While these techniques offer promise of a reagentless detection scheme, they often suffer from false readings caused by variable flow rates, changes in pH, or fluctuations in temperature.

The development of a reliable, reagentless inexpensive and miniaturized bio-chip for detection of biohazards in real time would represent a significant advance in the area of public health and safety.

SUMMARY

The invention provided a novel method for detection of analytes, particularly biohazards. A microarray containing immobilized sensing molecules captures complementary analytes on a redundant patterned substrate. Pattern analysis is performed using a computer algorithm.

A liquid or airborne sample is contacted with a substrate surface that includes least one microarray containing multiple positive array elements arranged in a redundant pattern on the substrate surface. The positive array elements contain sensing molecules that target the analyte. A plurality of microarrays can be employed, which microarrays can be the same or different (different microarrays can contain positive array elements that contain different sensing molecules, or they can have array elements arranged in a different pattern, or both). For example, positive array elements in a first microarray can contain a first sensing molecule targeting a first analyte, and positive elements in a second microarray can contain a second sensing molecule targeting a second analyte.

The sample can be applied in a batch mode to the substrate surface, or it can be flowed over the substrate surface. The substrate surface is preferably planar or, in the case of a sample that is flowed over the surface, contains a channel in which the microarray is disposed. The sample may be introduced into the channel as a point source, via side entry, or in any other way.

The sample is contacted with the microarray for a time and under conditions to cause the analyte to detectably interact with, e.g., to bind to, the sensing molecules. Detection of a redundant pattern on the substrate surface is indicative of the presence of analyte in the sample. A periodicity in the pattern can be detected, preferably through the use of a computer algorithm but also in some instances visually or through other means.

Optionally, the microarray also includes multiple null array elements that do not specifically target the analyte. The shape of the positive array elements on the substrate surface is preferably different from the shape of the null array elements. By assessing the interaction of non-targeted analytes with the positive array elements, and/or the interaction of targeted analytes with the null array elements or other parts of the substrate surface, the specificity of the targeted analyte for the positive array elements can be evaluated.

The sensing molecule is preferably a biomolecule, such as a protein, glycoprotein, nucleic acid or carbohydrate. The targeted analyte is preferably a biomolecule or a pathogenic organism such as a bacterium, virus or protozoan.

In a preferred embodiment, an analyte is detected by providing a substrate surface that includes one or more microarrays, preferably within a channel; flowing a sample containing the analyte over the substrate surface such that the sample sequentially contacts positive array elements in the microarray under conditions to cause the analyte to interact with the sensing molecules; and detecting the redundant pattern. In addition to the positive array elements, the microarray optionally includes multiple null array elements that do not specifically target the analyte. Likewise the substrate surface may include alternating regions in which the microarray is present or absent, such that the sample flow sequentially contacts the alternating regions. In any of these embodiments, the sequentially contacted positive array elements can be analyzed to determine concentration of the analyte in the sample. If desired, the sequentially contacted microarray regions also be analyzed to determine the level of nonspecific binding of sample components to array elements.

Another preferred embodiment for detecting an analyte utilizes a device that includes a channel having a surface that contains a plurality of positive array elements, or a plurality of microarrays, that transect the channel and are disposed sequentially along a length of the channel. The positive array elements or microarrays can be the same or different. A sample that contains an analyte is flowed through the channel such that the sample flow sequentially contacts the positive array elements under conditions to cause the analyte to interact with the sensing molecules, and the resulting redundant pattern is detected. The sequentially contacted positive array elements can be analyzed to determine concentration of the analyte in the sample.

Another preferred embodiment is useful for detecting the presence of multiple analytes having very different concentration levels in a sample. The sensor device contains a branched channel the includes a first branch having a surface that includes a plurality of microarrays containing positive array elements that target a first analyte and a second branch having a surface that includes a plurality of microarrays containing positive array elements that target a second analyte. A sample containing the first and second analytes is flowed through the branched channel such that a first amount of the sample flow enters the first branch and a second amount of the sample flow enters the second branch. For each branch the redundant pattern is then detected. This method is especially useful to detect analytes when concentration of the first analyte in the sample is at least an order of magnitude higher than the concentration of the second analyte. In that case, a larger amount sample flow is directed second branch, which contains positive array elements that target the analyte of lower concentration.

DETAILED DESCRIPTION OF THE ILLUSTRATIVE EMBODIMENTS

The present invention provides a method and device for detecting analytes, such as proteins, toxins, viruses or bacteria, that uses immobilized sensing molecules to capture the analytes on a patterned substrate. The device is particularly useful in detecting viral and bacterial pathogens, which can be captured directly from solution. The method is reagent free and allows real time detection of analytes. The patterned microarrays maintain their highly specific activity for weeks, and are ideally suited for the detection of multiple-threat biohazards. The device can be advantageously fabricated as a miniaturized biosensor, such as microchip, capable of detecting a wide variety of pathogens and other biohazards.

The present invention is based on the detection of intermolecular interactions (e.g., immunosystems such as antibody-antigen binding). The device is functionalized, in a patterned array, with at least one sensing molecule, such as a protein, that interacts with an analyte. An "array" or "microarray" as the term is used herein, is composed of multiple discrete (noncontiguous) positive array "elements" arranged in a periodic manner. The area within the array that does not contain positive array elements is called the background or the "null" array element. A checkerboard pattern, for example, contains alternating positive and null array elements. Note that when the term "element" or "array element" is used herein without further modification, it refers to a positive array element.

The array elements themselves can have a shape (e.g., a line, a square or a circle within which multiple sensing molecules are deposited) or they may be so small as to be a digital point element (e.g., only one or a minimal number of sensing molecules). The overall shape into which the array elements themselves are arranged constitutes the "pattern" of the array. For example, an array of sixteen elements arranged in four columns and four rows such that the elements are equidistant from each other would form a square "pattern." In the device of the invention, sensing molecules deposited in discrete positions on the substrate constitute the multiple positive "elements" of the array, and the topographical arrangement of these positive elements on the substrate surface forms the pattern.

Figure 1:
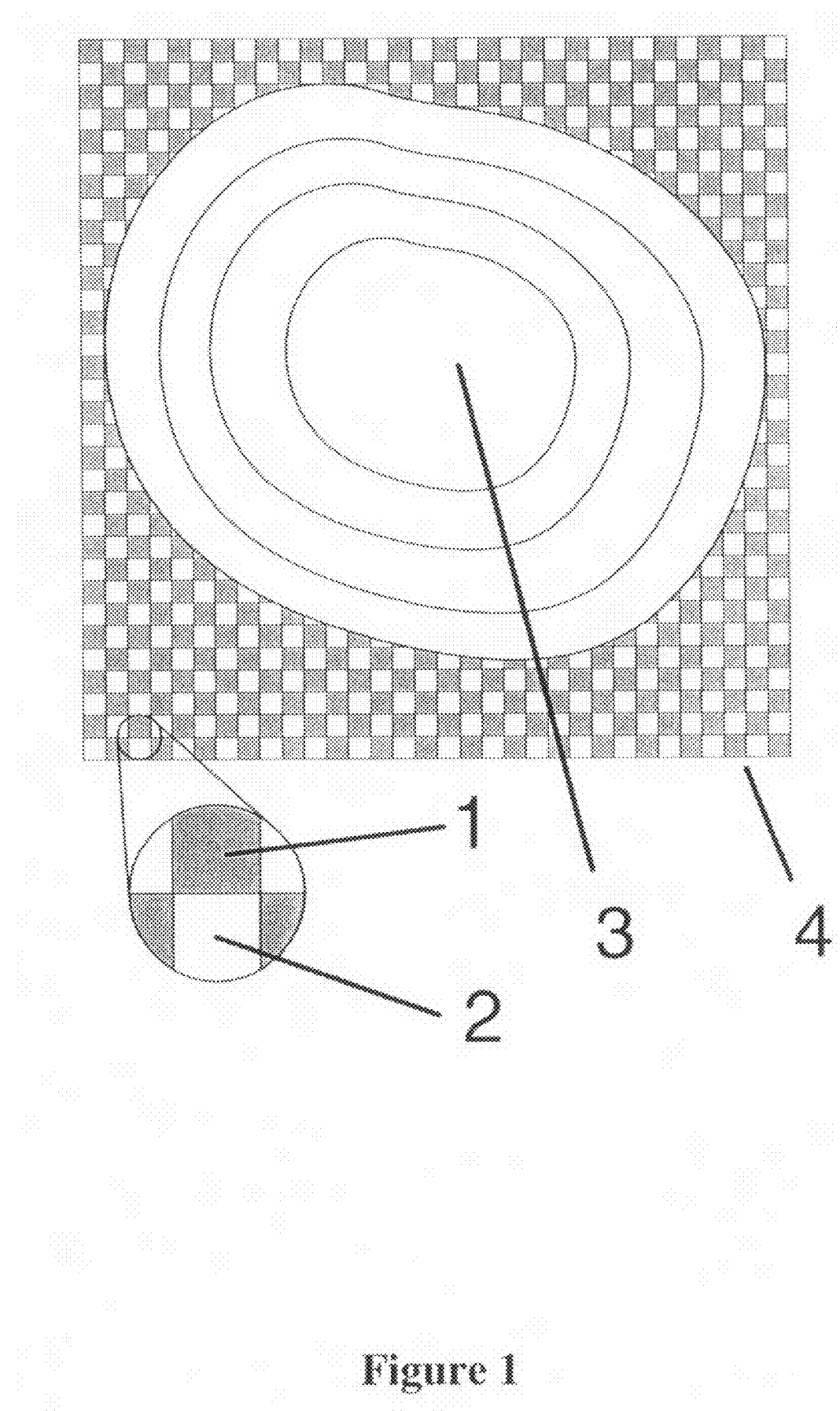
FIG. 1 shows a liquid sample in contact with a redundant microarray of the invention.

FIG. 1 shows a representative microarray according to the invention. Positive array elements 1 are interspersed with null array elements 2 to form a homogenous array 4 in a checkerboard pattern. The sample 3 is contacted to the array surface.

The interaction of the analyte with the sensing molecule on the active surface of the device produces a change that is detectable through a transducing mechanism (e.g., impedance, mass change, etc.). The repetitiveness or redundancy in the array of sensing molecules increases the limits of detection by averaging a large number of binding events and permitting the use of pattern recognition algorithms.

The invention provides both a method for detecting an analyte, and a device for detecting an analyte. When the analyte to be detected is a biological molecule, such as a pathogenic microbe, the device is termed a biosensor. The device is especially useful for detecting biological threats and will find application in military, medical, food quality and environmental venues. Advantageously, the method and device of the invention allow bacteria can be captured directly from solution onto an antibody microarray.

Surface Deposition and Patterning

The biosensor device contains a substrate (also referred to herein as a "transducer") onto which the sensing molecules are deposited. Substrates can be fabricated from a number of different materials such as gold, silver, silicon, polymers, glass and indium tin oxide (ITO). The choice of substrate depends, at least in part, on the detection method chosen. For example, if electrochemical detection is to be used, the substrate is preferably fabricated from gold or ITO. On the other hand, if optical detection methods are to be used, glass and silica are good inexpensive choices for the substrate material.

In most applications, the substrate surface is pretreated prior to deposition of the sensing molecule. The type of pretreatment depends on whether the sensing molecule is to be attached to the substrate surface covalently or noncovalently. If the sensing molecule is to be attached by physical adsorption (a noncovalent interaction) for example, a glass substrate can be silanized to make it hydrophobic by covering it with long hydrocarbon chains. Likewise a gold surface can be treated with a long chain aliphatic thiol to facilitate adsorption of the sensing molecule, such as a protein. If the sensing molecule is to be attached covalently, the substrate surface must be functionalized with a reactive group that chemically bonds with the sensing molecule. A glass substrate, for example, can be pretreated with a silane that has a reactive group (e.g., a carboxylic acid or an amino group) at the end of the aliphatic chain. A gold substrate, on the other hand, can be pretreated with a long chain mercaptoacid which presents a carboxylic acid for reaction with the sensing molecule. Covalent attachment of the sensing molecule is preferred for electrochemical detection methods.

Proteins and other capture molecules can be deposited onto the substrate, typically from aqueous solution, using any deposition method that can be controlled to form uniform molecular arrays on the substrate. For example, deposition can be accomplished using microfluidic networks, inkjet deposition, microcontact printing, optical (photo) lithography, micromachining, laser based methods and electrochemical methods. The deposition method should be coordinated with the detection method to be used. For example, arrays with very small elements (e.g., 1 µm×1 µm) can be analyzed using electrochemical detection methods but probably not spectroscopic methods, which lack the necessary resolving capacity.

In one embodiment, patterning proteins such as antibodies into a microarray is accomplished by the use of microcontact printing (µCP). The µCP method has been used to pattern a variety of different proteins (Kane et al. (1999) Biomaterials, 20, 2363; Bernard et al. (2000) Adv. Materials, 12, 1067; Ostuni et al. (1999) Colloids and Surf. B, 15, 3; Bernard et al. (1998) Langmuir, 14, 2225; James et al. (1998) Langmuir 14, 741; Lahiri et al. (1999) Langmuir, 15, 2055; Lopez et al. (1993) J. Am. Chem. Soc., 115, 10774; Inerowicz et al. (2002) Langmuir, 18, 5263) without loss of biological activity. Also known as a "soft lithography technique", µCP has in addition been successfully applied to pattern cells. Microcontact printed substrates have also been used in cell biology studies to capture cells at specific sites and then grow them as they adhered to the surface (Zhang et al. (1999) Biomaterials, 20, 1213; Singhvi et al. (1994) Science, 264, 696).

Microcontact printing (µCP) is achieved using a Si master containing a particular patterned relief (with micrometer dimensions) as a mold for an elastic polymer such as polydimethysiloxane (PDMS). By letting the polymer cure on the mold, an inverse of the mold's relief is transferred to the harden polymer. The hardened polymer can now be used as a stamp by simply inking the high relief with a protein of interest and pressing the stamp against a prepared surface, thereby transferring a pattern of proteins onto the surface. The µCP technique is useful, since the mold can be lithographically defined creating a stamp capable of patterning proteins on the micrometer length scale. One disadvantage of the µCP technique is the inability to pattern multiple-protein on a 100-micron length scale because the stamp dimensions are too large to achieve that level of resolution. To accomplish multiple-protein patterning requires different deposition techniques such as microfluidics.

Figure 2:
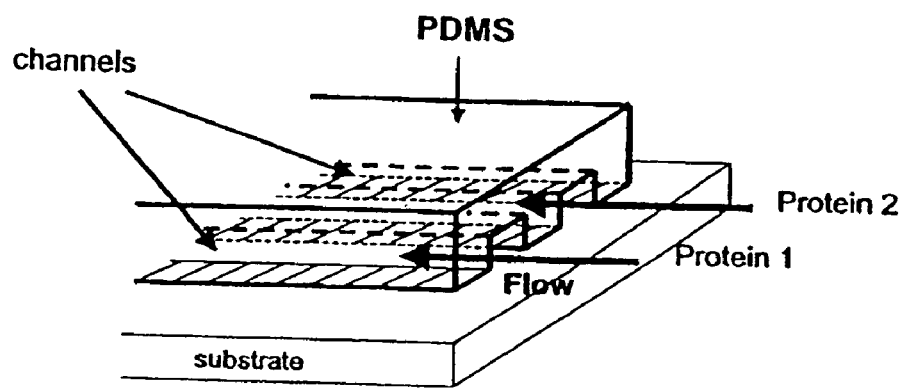
FIG. 2 shows a microfluidic network (μFN): a) a patterned elastomer forming a μFN by contact with a substrate allowing delivery of a solution of biomolecules to the substrate, b) flow of liquid between the filling pad and an opposite pad fills the array of microchannels and c) assembly of different zones of flow on the substrate surface results from the independence of capillaries; each requires only a small volume (about 1 μL) of liquid to fill (left panel, top view; right panel, side cut along the channel).
Figure 2:
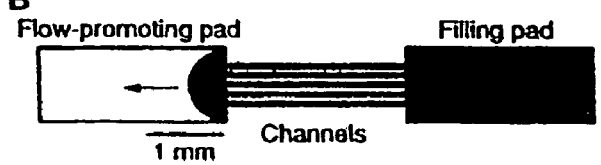
Figure 2:
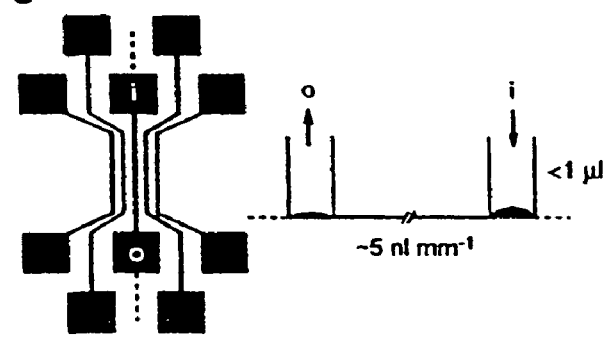

Recently, the use of microfluidic networks (MFN) has emerged as a useful technique for the deposition of multiple protein arrays on the micron length scale. FIG. 2 is a schematic of an example of an MFN deposition showing the basic concept of creating a small flow channel between a fabricated structure (containing the etched fluidic structures) pressed against the prepared substrate to form a sandwich-type structure. The sensing molecule is deposited onto the prepared substrate surface in a thin line by flowing a solution of the molecule through the channel. It is possible to create these fabricated structure containing these fluidic channels from various materials such as SiO, Au and PDMS. Each of these materials has its own unique preparation requirements since they are not ideal surfaces for microfluidics (i.e., they are not hydrophilic). For example, to create a hydrophilic PDMS surface requires a treatment in an oxygen-plasma cleaner.

Despite the necessity of rigorous surface treatment, PDMS is an inexpensive and flexible material to use in MFN since the fabrication is similar to creating a PDMS microcontact stamp. Therefore, multiple fluidic channel stamps can be cast from the same master mold with a minimum effort; unlike channel fabrication in Si which requires mass lithography. In addition, PDMS can be easily sealed onto various surfaces due to its flexibility and adhesive nature.

A drawback to using PDMS derives from its tendency to nonspecifically adsorb proteins from the solution flowing through the channel. To overcome this problem, a surface treatment that blocks the protein adsorption is required after the channels have been etched into the fabricated structure but before placing it against the prepared substrate to form the flow channels in preparation for the deposition of the sensing molecule.

Structure and Topography of the Device

The invention is not limited by the size of the array elements or the distance between them, except that the array elements need to be large enough to be detectable, and separated by a sufficient distance to so as to be resolvable, using the detection method selected to detect the interaction event (such as the bound complex of the analyte and the sensing molecule). To accommodate currently available detection methods, the sensing molecules are preferably disposed in an area of at least about 1 µm$^2$. However, as nanotechnology progresses it is expected that limits of detection will continue to be lowered soon achieving "digital counting." It should be understood that the principles of the invention are not dependent on the detection mechanism or the array size, and will continue to apply as the limits of detection are pushed further. The distance between the elements is typically of the same scale as the size of the elements themselves, but can be smaller or larger as indicated by the particular application. When the analyte to be detected is a bacterium, the size of the microarray elements can, if desired, be selected such that only one bacterium will bind per array element.

The invention is not limited by the number of elements in the microarray (the redundancy), and in some applications (like the long channels described below) the microarrays can include hundreds, thousands or even millions of elements. A typical channel is 100 µm-1 mm wide and has array elements with a dimension of about 10 µm distributed within the channel at about 10 µm increments. At a minimum the microarray should include at least 4 elements, more preferably at least 10 elements. There is no limit to the number of microarrays a sensing device can include, nor is there any limit to how many different analytes can be detected. If multiple analyte detection is desired, multiple microarrays can be used, each having the elements arranged in a unique pattern and/or such that the different microarrays are located at different positions on the device, so as to allow the different regions binding to the different analytes to be distinguished. When small microarrays are used (e.g., 50-100 µm$^2$) hundreds or thousands of different analytes can be detected on a surface of only a few square millimeters.

The invention is not limited by any particular pattern for the microarray of positive array elements. A pattern that lends itself to Fourier transform or other pattern recognition algorithm, for example a repeating symmetric pattern that produces a series of squares (checkerboard), triangles, crosshatches, circles, stripes and the like, is suitable. The more complicated the pattern, the more stringent the test. In a preferred embodiment, the positive array elements and the null array elements are shaped differently (i.e., they do not appear identical to the detector); this is what is referred to herein as a "nonuniform" pattern. For example, a checkerboard is a "uniform" pattern because the positive array elements and the null array elements are both squares of identical size. However, an array consisting of many rows of "plus" marks as positive array elements (with the null "elements" constituting the grid-like surface area between the "pluses") would be a "nonuniform" pattern. The repeating pattern can be linear or two-dimensional. The substrate surface is typically planar or in the form of a channel.

In devices that contain multiple sensing molecules, the sensing molecules may be confined to a homogeneous region of the device, and arrayed within that homogeneous region. Alternatively, regions containing the different sensing molecules may be interspersed and thus become part of a heterogeneous linear or two-dimensional array. Patterns used to array two or more sensing molecules within the same device can be the same (for example, in devices having different regions assigned to different sensing molecules) or they may be different, which may be convenient when the regions containing the different sensing molecules are interspersed.

As an example, the device can include a channel having a first microarray containing first sensing molecule adjacent to a second microarray containing a second sensing molecule. As an aqueous sample flows through the channel, it will contact the first microarray followed by the second microarray. The device can then be analyzed to determine whether a detectable pattern is seen for either the first or second microarray, or both, thereby indicating the presence of a first or second complementary analyte, or both, respectively.

The device can be customized for many different applications. For example, the device can contain a channel that is long enough to provide information about the concentration of an analyte in a sample flowing through it after being calibrated using sample containing a known concentration or amount of an analyte. The sample is run through the channel, and the channel is interrogated for the presence of a bound analyte at different points along its length, preferably using a pattern recognition algorithm. The point at which the analyte is no longer detectable can be used to obtain its concentration by comparing it to the calibration. An analyte that is binding nonspecifically to the array elements, on the other hand, might be expected to show relatively constant binding along the length of the channel.

In one embodiment, a microarray is disposed along the entire length of the channel. In another embodiment, the channel contains alternating regions along its length in which the microarray is present or absent. An example of this latter embodiment is a channel that is transected by multiple thin perpendicular positive array elements or microarray regions. The transecting array elements, which are very narrow compared to the width of the channel (e.g., a 2 µm wide microarray region compared to a channel width of 200 µm) are separated by regions in the channel that are free of the microarray. A liquid sample is introduced into the channel, and as it flows through it, the complementary analyte is progressively removed from the sample through repeated, sequential contacts with sensing molecules in the array elements. An analyte the binds the sensing molecule in the array elements will eventually no longer be detectable as the channel is interrogated along its length; on the other hand, a nonspecific analyte would not be expected to show progressively lower binding levels along the length of the channel. Furthermore, if the sample is introduced as a point source, the sequential, narrow band microarray regions can also be analyzed to determine the amount of spreading that occurs as the sample progresses down the channel. Spreading is dependent on the diffusion coefficient of the analyte and can aid in its identification.

Figure 3A:
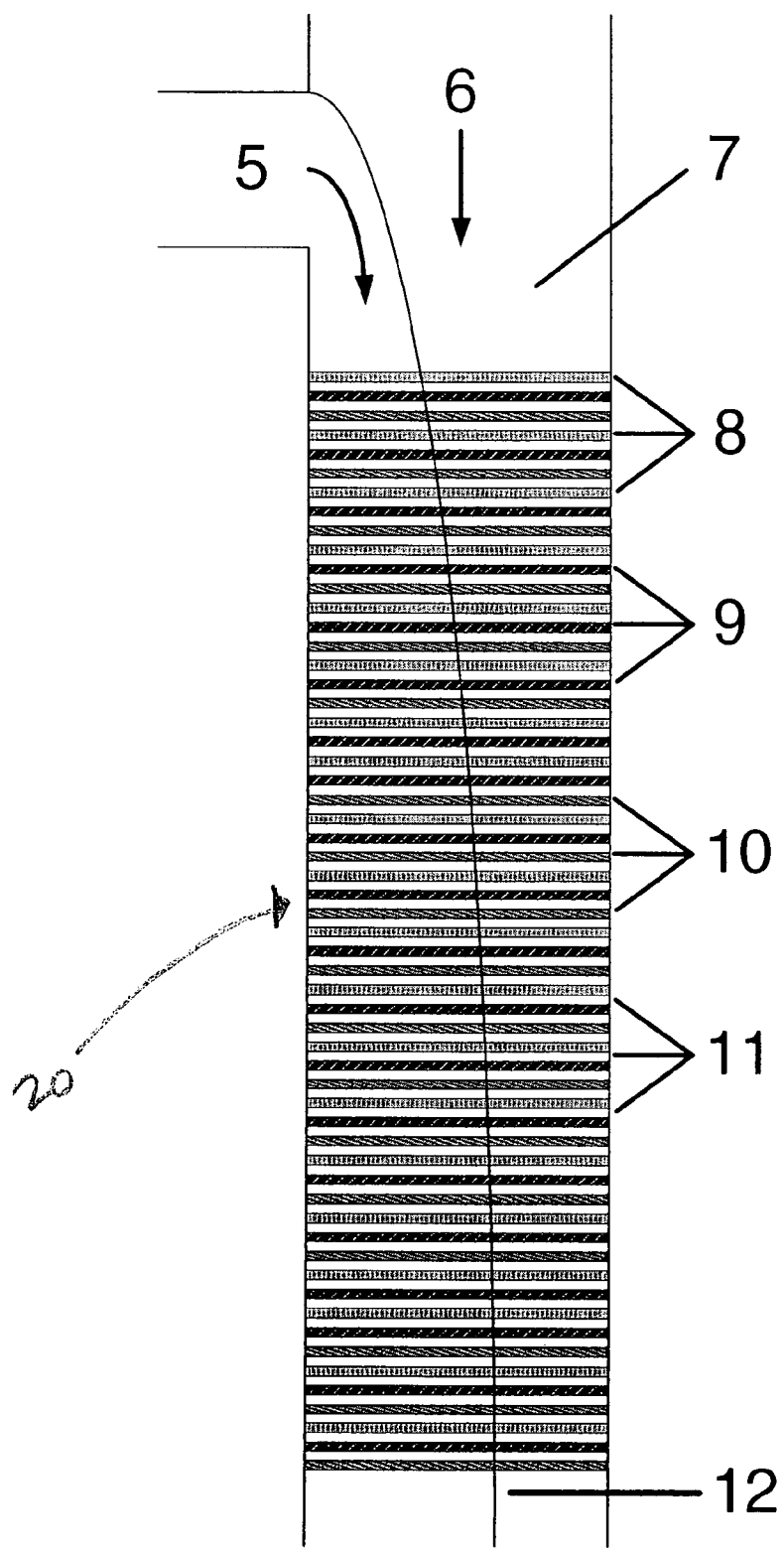
FIG. 3 shows a channel containing a redundant microarray that detects multiple analytes: a) flow of sample through the channel, b) concentration of representative analyte in a channel cross section following introduction of sample through a side port, and c) for analytes having different relative concentrations in a sample, histogram of relative analyte concentrations along the longitudinal length of the channel.

Optionally, the long channel can contain multiple alternating microarrays or array elements having different sensing proteins to detect and quantify multiple analytes in a multiplexed method. The same sample can be assayed for the presence of a number of different analytes. FIG. 3a shows channel 20 containing three different alternating array elements 8, 9 and 10, separated by null array elements 11 to form a microarray capable of detecting analytes A (via array element 8), B (via array element 9) and C (via array element 10). Sample is introduced into the channel at analyte inlet channel 5, and buffer is introduced into buffer inlet channel 6. As it flows through channel 20, the sample stream exhibits a longitudinal dispersion 12. FIG. 3b shows the lateral concentration 13 of an analyte across a complementary array element compared to the lateral concentration 14 of an analyte across a null element. FIG. 3c is a histogram charting the relative concentration 15, 16 and 17 of analytes A, B and C, respectively, at individual array elements along a longitudinal length of channel 20 near the analyte entry side of the channel, showing that [A]<[B]<[C].

Another customized application allows the device to be used to detect analytes in a fluid sample that may vary greatly in concentration within the sample, even by orders of magnitude. Fluid flow can directed to a branch point which splits it into two or more smaller streams. A small portion of the fluid is channeled to a microarray containing sensing molecules selected to detect an analyte expected to be in high concentration in the sample, and a larger portion of the fluid is channeled to detect an analyte expected to be in much smaller concentration. The amount of flow directed into any branch or subchannel can be determined as a function of the concentration of analyte expected in the sample. Also, as discussed earlier, if the channel is long enough to bind most of the analyte in the sample, the concentration of the analyte can be determined.

Sensing Molecules and their Analytes

The device of present invention identifies the presence of an analyte by detecting an interaction between a sensing molecule and the analyte. An analyte that interacts with a sensing molecule is sometimes referred to herein an analyte that is "complementary" to that sensing molecule. The invention is not limited by the analyte to be detected. Biological analytes such as proteins, nucleic acids, carbohydrates, viruses, cells and cell fragments, including microbial pathogens such as pathogenic bacteria and protozoa, can be detected according to the method of the invention. Likewise nonbiological analytes such as chemical toxins can be detected provided they are capable of detectable interaction with a sensing molecule. A representative list of biological agents that can be detected using method and device of the invention is found in the book "Chemical and Biological Terrorism Research and Development to Improve Civilian Medial Response," published by the Institute of Medicine, National Research Council; National Academy Press; Washington D.C. (1999).

The choice of sensing molecule depends, of course, on the analyte to be detected. And, as noted earlier, the device can include a single sensing molecule or multiple sensing molecules. If the analyte is a biological analyte, the sensing molecule can, for example, be a protein, such as an antibody or a receptor, or a nucleic acid, such as DNA or RNA. A particularly useful interaction in the method of the invention is the naturally occurring biomolecular interaction between an antibody and an antigen (immunosystem). As another example, if the analyte is protein or nucleic acid capable of binding a ligand, or a cell expressing a membrane receptor capable of binding a ligand, the sensing molecule can be the ligand. In a particular advantageous embodiment, the sensing molecule used to detect a pathogenic organism such as a virus or bacterium constitutes a "host recognition substance" such as an oligosaccharide, a glycoprotein, a siderophore or the like. These substances are used by the pathogen to identify its host and are thus very important to an organism's survival. While a bioterrorist might genetically alter the coat proteins on a pathogenic organism to avoid detection, it would be difficult to make changes in the organism's host recognition system. Thus, detection mechanisms that are able to sense these "host recognition substances" are considered to be "evasion-proof" sensing systems. Semiochemicals, naturally occurring "message" bearing biochemicals used organisms for communication and perception of their environment, can also be detected using the method and device of the invention. They include pheromones, kairomones and allomones.

The interactions between the analyte and the sensing molecule can be covalent or noncovalent. Noncovalent interactions include ionic, hydrophobic and Van der Waals interactions. For example, interactions among complementary nucleic acids (also known as nucleic acid hybridizations) are noncovalent. Preferably the interaction between the sensing molecule and the analyte is sufficiently specific to distinguish the analyte of interest from at least some other analytes that may be present in the sample. The degree of specificity can be predetermined by the investigator.

In one embodiment, an activated substrate is prepared that is potentially useful for binding many different substrate molecules. A nucleic acid, preferably DNA, is deposited onto the substrate surface to form an activated surface comprising the array elements. This activated surface can then be used to link (tether) any desired sensing molecule, provided that the complementary DNA has been covalently attached to the sensing molecule.

Although the device is especially well suited for detecting analytes in aqueous samples, it can be modified for use in detecting analytes in air or in body fluids.

Sample Application

The device of the invention can be used to detect analytes in either batch mode or a flow mode. In batch mode (e.g., FIG. 1), the active surface is contacted with a sample suspected of containing one or more analytes that bind to the sensing molecule(s) on the device surface for a predetermined exposure time. For example, the device can be submerged in a water supply for a predetermined length of time to test for the presence of biohazards. In flow mode (e.g., FIG. 3), a sample is passed over the active surface in a liquid flow. The sample may be passed over a planar surface or through a channel. The channel may be an open channel or a closed channel, such as a column. The flow may be discrete (i.e., a defined volume of liquid) or continuous. Intermittent operation of the device in flow mode can be used advantageously to quantify the amount of one or more analytes in a sample as described above.

Liquid samples, particularly aqueous samples, are preferred, but the method and device can also be used to analyze airborne contaminants. The moisture content in air is typically high enough to adequately hydrate the substrate surface and facilitate the interaction between a biological analyte, such as a pathogenic organism, and the sensing molecule, such as a protein (e.g., an antibody or an enzyme).

Analyte Detection (Signal Transduction)

Analytes bound to the sensing molecules can be detected using any convenient method. Detection methods included optical or spectroscopic methods such as fluorescence, UV detection, phosphorescence, diffraction-based methods, CCD imaging, and the like; chemical or enzymatic methods such as enzyme-linked immunosorbant (ELISA) assays; optical microscopy, transmission or scanning electron microscopy, or atomic force microscopy; mass change; and radiometry. The invention is particularly well suited to the use of topographical methods of detection, such as scanning probe microscopy (SPM). Electrochemical detection of analytes in liquid samples is also facilitated by the present invention, allowing for a "frontline defense" in the threat of biological warfare. Capacitance can be measured using conducting electrodes, for example, using gold or indium tin oxide (ITO) electrodes. In capacitive biosensors interdigitated electrodes (IDE) can be used, as can parallel plate electrodes. Impedance can be measured using a gold or ITO electrode.

High resolution scanning probe microscopy (SPM) is a preferred method for detecting the presence of captured bacteria. Advantageously, this approach allows direct interrogation of the physical features of captured bacteria. Topographical features of bacteria can be very unique and aid in confirming their presence. The high lateral resolution of current SPM technology can lower the limits of detection, since theoretically the presence of a single bacterium can be determined from an SPM image.

Analytes can be detected directly (for example, by using SPM to detect bound bacteria; or using radiometric methods to detect radioactive analytes) or indirectly (for example, by using a fluorescent antibody to detect a bacterium or other antigen). Another method for indirectly detecting an interaction of the analyte with the sensing molecule is the detection a change to the sensing molecule caused by the analyte, even if the analyte does not, in fact, bind to the sensing molecule. For example, the analyte can cause a detectable chemical change in the sensing molecule, a cross-linking of sensing molecules, and the like.

Advantageously, bound analytes can be further processed to identify or quantify the analytes. They can be eluted from the substrate and further characterized, or they can be further characterized directly on the substrate surface. Elution of the bound analyte allows the analyte to be conveniently isolated and concentrated, just as in liquid chromatography.

Some detection methods, such as optical methods, advantageously allow for continuous monitoring of a fluid flow. If analyte capture exceeds a certain level, the system can alert the operator. This type of system is useful to monitor water supplies, for example.

Pattern Analysis

A benefit of patterning analytes in a microarray is the possibility of highly sensitive, rapid detection through pattern recognition algorithms. Advantageously, microarray redundancy (pattern formation) effectively increases the signal to noise ratio and lowers the limit of detection. Images, such as CCD images, can be processed, for example using Fourier transforms or other pattern recognition algorithms to identify the presence of a certain pattern of bound analytes. The parameters of the transformation can be used to determine various pattern parameters such as the periodicity and, optionally, shape of an observed pattern, which are then are compared to the known pattern of deposition of the sensing molecule. If the two are essentially the same, this confirms the presence of the analyte in the sample. If desired, the computer can then be given the additional information, such as the actual size of the array elements, and by evaluating the image in view of the additional information can determine the levels of specific and nonspecific analyte binding.

By facilitating the use of pattern recognition algorithms, the use of patterned microarrays increases the limit of detection of the analyte compared to the use of nonredundant analyte binding methods, particularly in the presence of non-specific binding, whether in the form of a targeted analyte binding to nonfunctionalized areas or a non-targeted analyte binding to functionalized areas. Specificity can be assessed, for example, by comparing the number of targeted analytes detected per unit area for the positive array elements to the number of targeted analytes detected per unit area for the other regions of the microarray (e.g., null array elements and/or other nonfunctionalized regions).

EXAMPLES

The present invention is illustrated by the following examples. It is to be understood that the particular examples, materials, amounts, and procedures are to be interpreted broadly in accordance with the scope and spirit of the invention as set forth herein.

Example I

Redundant Patterned Protein Microarrays for Bacterial Detection

Patterned microarrays of antibodies to specific bacteria were used to perform a series of bacterial immunoassays of *E. coli* 0157:H7 and *Renibacterium Salmoninarum* (RS). Microarrays were fabricated using microcontact printing (μCP) and characterized using scanning probe microscopy (SPM). The high-resolution SPM imaging showed that bacteria had a higher binding affinity to antibody patterns than unfunctionalized regions of the substrates. Additional studies indicated a low binding affinity when bacteria were exposed to microarrays of non-specific antibodies.

Materials and Methods

Stamp fabrication. Poly(dimethylsiloxane) (PDMS) stamps were fabricated by casting and curing Sylgard 184 (Dow Corning, Midland, Mich., USA), an elastomeric polymer, against photoresist micropatterned silicone masters. The master relief pattern used to make a PDMS stamp was a negative relief of the stamp mold and was manufactured at the Stanford University Nanofabrication Facility. These masters were made by first spin coating a positive photoresist, SPR 220-7 from Shipley (Marlborough, Mass., USA) on a silicon wafer. Irradiation with UV light through a chromium mask was used to render any exposed photoresist soluble, which was then removed by washing with the developer LDD26W from Shipley (Marlborough, Mass., USA). The patterns used for our experiments consisted of a 10 μm×10 μm square pattern with a 5 μm separation between squares on all sides. The PDMS stamps were cured for 2 days at room temperature or 12 hours at 60° C. and sonicated in an ethanol-water solution (1:2) before oxidation in a commercially available plasma cleaner.

Chemicals and reagents. Immunoassay reagents included affinity-purified antibody to *Escherichia coli* 0157H:7 (*E. coli*), affinity purified antibody to *Renibacterium Salmoninarum* (RS), as well as positive controls of *E. coli* 0157H:7 bacteria and all RS bacteria. Control sample were obtained from Kirkegaard & Perry Laboratories, (Gaithersburg, Md., USA). The positive control bacteria used in our work were heat killed. Although the bacteria are dead, studies conducted in solution still showed specific antibody binding. Bovine serum albumin was purchased from Sigma (St. Louis, Mo., USA). Tween, chlorodimethylooctadecylsilane and anhydrous toluene were obtained from Aldrich (Milwaukee, Wis., USA) and used without further processing.

Substrate preparation. Functionalized substrates used for this study were glass slides (Gold Seal, Hungary) coated with silane. Protein antibodies to the targeted bacteria were immobilized on these substrates by physical adsorption to the silane layer. The glass slides were chosen because they are inexpensive, transparent and a good material on which to deposit the proteins. Preparation of the glass substrates is described in detail elsewhere (Inerowicz et al. (2002) Langmuir, 18, 5263). The substrates were cleaned with sulfochromic acid and silanized in a solution of chlorodimethyloctadecylsilane (0.02 M) in an anhydrous toluene solution (Duchet et al. (1997) Langmuir, 13, 2271). The RMS surface roughness of the glass substrates used in this study was found to be ~1.3 nm using an SPM. The roughness of the substrate plays a critical role in the rapid determination of relevant topographical changes when imaging with SPM after exposure to bacteria.

Microcontact printing (μCP). The PDMS elastomer is a common choice for microcontact printing (μCP). Hydrophobic PDMS surfaces can be made hydrophilic by an appropriate treatment. This is accomplished by placing the stamp in a plasma cleaner (Harrick Scientific, Ossining, N.Y., USA) prior to use. Thus treated PDMS is an acceptable material for the directed transfer of proteins from solution to a micropattern on a solid substrate. The process of loading a protein onto a PDMS stamp will be referred to as "inking" and the protein loaded onto the stamp or substrate as the "inking protein".

The surface of the PDMS stamp was exposed to solutions of inking antibodies for various lengths of time. The concentrations of inking antibodies to bacteria were in the range of 100-200 μg/ml ($6.6 \times 10^{-7}$-$1.3 \times 10^{-6}$ M). All antibodies solutions were made in phosphate buffer saline (PBS) at pH=7.4. After 10 to 30 minutes, excess solution was removed and the stamp was dried under a stream of nitrogen gas. After inking, the stamp was brought into contact with the glass substrate and a small force was applied to make a better contact between both surfaces. The stamp was removed after approximately 1 minute and the glass slide washed with PBS followed a deionized water wash.

Imaging the patterned array of antibodies with the SPM optimized this entire process. Both topographical and phase-contrast imaging were employed to determine if the desired micron-size pattern of antibodies had been faithfully transferred to the silanized substrate.

Performing the bacterial assay. The substrates with printed microarrays of antibodies were incubated in a solution containing complementary bacteria. To prevent non-specific adsorption to regions between the antibody arrays, bovine serum albumin (BSA), Tween 20 or Tween 80 were used as backfilling agents. The concentration of BSA was 5-10 mg/ml ($10^{-5}$-$10^{-4}$M); the typical concentration of Tween was 0.1-0.5%.

Figure 4:
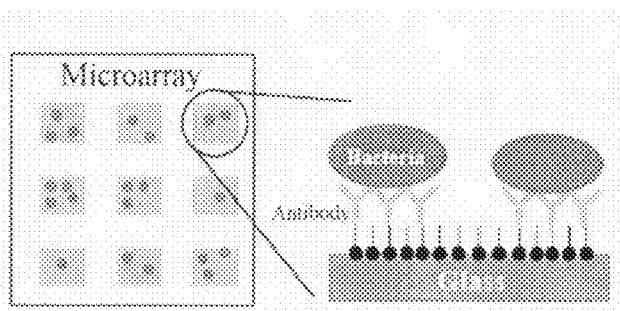
FIG. 4 shows a schematic of bacterial binding to a checkerboard patterned microarray of antibodies that bind the bacteria.

The substrates with patterned antibody were incubated with an analyzed solution containing complimentary bacteria for 30-40 minutes and washed with phosphate buffer and water before microscopic and SPM studies. Concentration of the original stock solution of heat-killed *E. coli* and RS was approximately $7.0 \times 10^9$ cells/ml and $3.0 \times 10^9$ cells/ml respectively. Before incubation with the antibody array, the bacteria were diluted 1:100 or 1:1000 with phosphate buffer (0.01M) pH=7.4. A schematic representation of this particular immunosystem is given in FIG. 4.

To determine the magnitude of cross-reaction between the two antibody-bacteria systems used for this study, antibody microarrays of *E. coli* were exposed to RS bacteria and vise versa.

Microscopy. An optical microscope was used to verify the performance of the immunoassay before utilizing more precise scanning probe techniques. A Nikon TE-300 optical microscope was used, at magnifications 50× or ×100× to investigate the emergence of detectable patterns on the substrates after exposure to bacteria. An attractive feature of this simple approach is that patterns of adsorbed bacteria can be seen directly.

Scanning probe techniques. Precise verification of the quality of printing and the efficiency of the bacterial-antibody binding were obtained using a PicoSPM scanning probe microscopy (SPM) system (Molecular Imaging™, Phoenix, Ariz.). The SPM system was modified to allow mounting on an inverted optical microscope, which greatly aided in the positioning of the SPM tip over the antibody arrays. The substrates were imaged in non-contact modes using a cantilever with a force constant of ~2 N/m (ThermoMicroscopes™ Non-Contact Ultralevers (ULNC-AUHW)).

Results and Discussion

Figure 5:
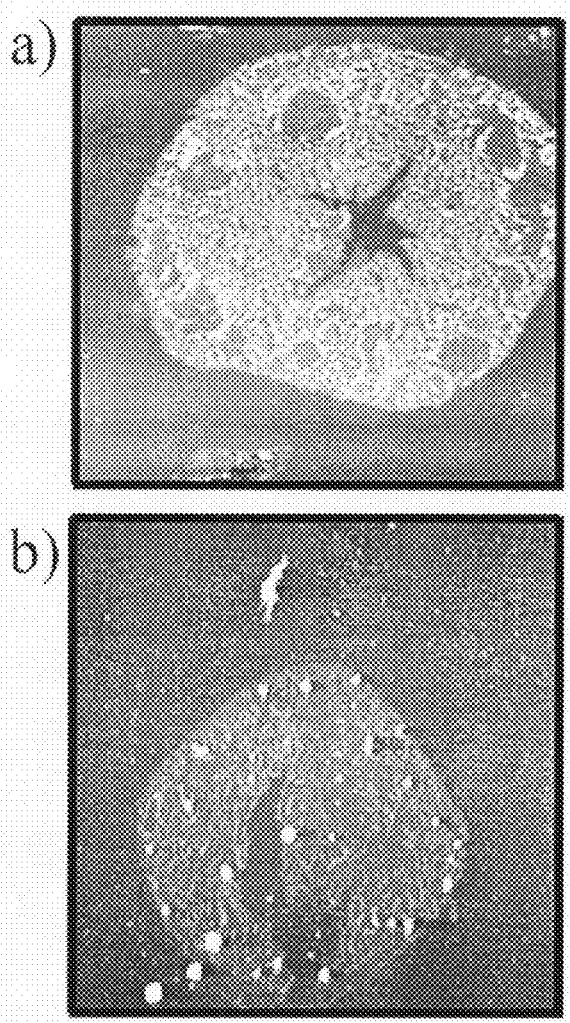
FIG. 5 shows noncontact topological scanning probe microscopy (SPM) images of antibody microarray of E. coli a) before incubation (scan size: 9 μm×9 μm) and b) after incubation with a solution of E. coli bacteria (scan size 14 μm×14 μm).
Figure 6:
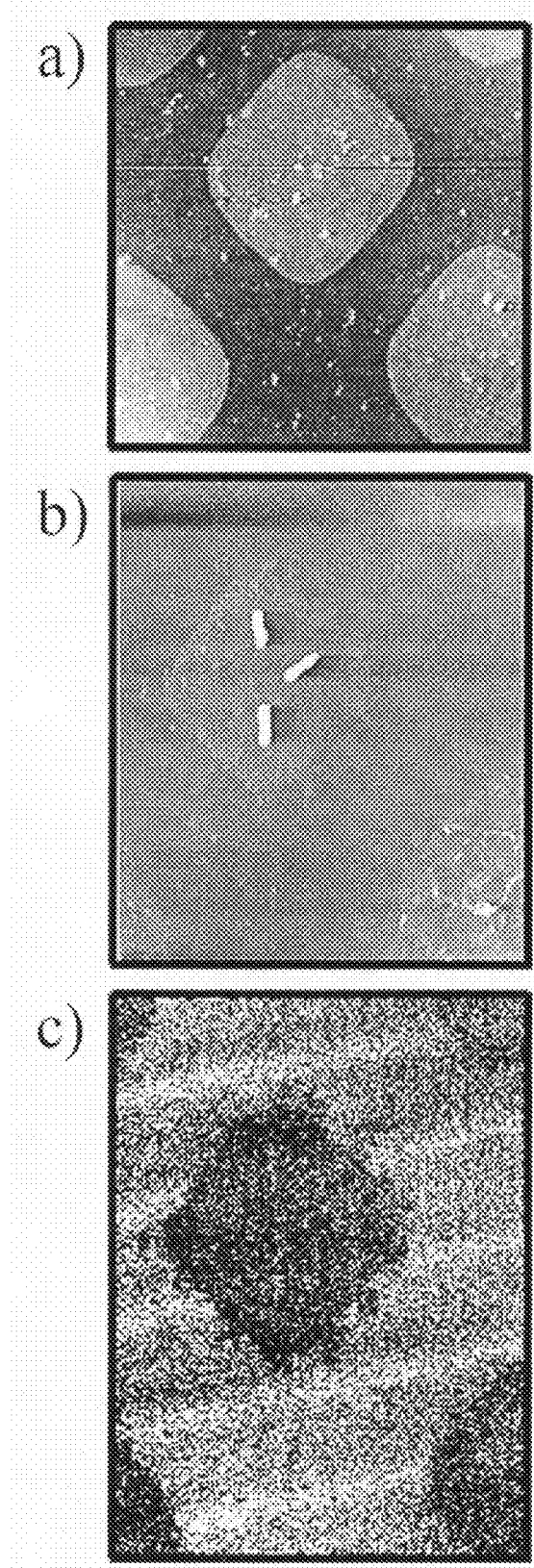
FIG. 6 shows noncontact topological SPM images of antibody microarray to Renibacterium salmoninarum (RS) a) before incubation (scan size 25×25 μm) and b) after incubation with a solution RS bacteria (scan size 21.5×21.5 μm); c) is an accompanying phase map to b).

FIGS. 5*a* and 6*a* show false-colored non-contact SPM topographic images of the immobilized antibodies to both the *E. coli* and RS bacteria before performing a bacterial assay. These images were used to confirm the quality of μCP antibody transfer. μCP fabricated arrays of both antibodies were observed to have a submicron sharpness.

The SPM imaging shows the height of the *E. coli* antibody is 6±3 nm (higher morphology results in a lighter color). Similarly the height of RS antibody is also found to be 5±2 nm. Both images show defects in the transferred antibody monolayers. The μCP antibody to *E. coli* consistently appeared to have micrometer-sized defects located in the center of the printed region. Other investigators have also reported this tendency for higher quality printing around the edges of micron-size patterns. Observed defects on the microarrays of RS antibody were on average much smaller (about 100 nm) than defects present in *E. coli* antibody arrays.

The area of the defects observed on both types of antibody arrays was relatively small compared to the total area coated by the antibody monolayer.

The images also show the absence of large foreign objects between the printed regions of antibodies. This control over the preparation of the patterned arrays is critical for a conclusive immunological identification and is only possible by optimizing each step in the array fabrication process. As an example, foreign objects present on the RS antibody array, before incubation, had an average height of about 10 nm and are much smaller than the measured height of the RS bacteria which typically are greater than 150 nm tall. We conclude that their presence will not adversely affect the determination of bacterial binding.

FIG. 5*b* is an SPM image of an antibody microarray to *E. coli* after incubation in a solution of *E. coli* bacteria at a concentration of $7 \times 10^7$ cell/ml. These images show the presence of large objects, with an average height of 130±40 nm. Most importantly, these objects are observed to have a tendency to selectively bind to the printed antibody regions.

The large objects attached to the printed antibody regions in FIG. 5*b* had a large distribution of topographic heights. This is to be expected due to the fact that heating killed the *E. coli* bacteria. This caused lysing of cells, which results in fragmentation of the bacterial cells into many small particles of random sizes. FIG. 6*a* is a larger scan of the *E. coli* antibody microarray after incubation. From the SPM images, it is estimated that about 4% of the antibody area is coated by the *E. coli* bacteria at this concentration during an exposure time of 40 minutes. This low coverage is consistent with recently published studies of electrochemical detection of *E. coli* (Ruan et al. (2002) *Anal. Chem.*, 74, 4814.)

FIG. 6*b* shows a noncontact SPM image of an antibody microarray to RS after exposure to a solution of RS bacteria at a concentration of $3 \times 10^6$ cell/ml. Unlike the *E. coli*, the RS bacteria had a more definite shape and size, making their identification easier. The average height of the RS bacteria was found to be 180±50 nm. FIG. 6*c* is a phase image made simultaneously with FIG. 6*b*. The phase image is useful for verifying the presence of the patterned antibody region which has a low contrast in FIG. 6*b* due to the large difference in the heights of the bacteria and antibody; it is often difficult in topographic imaging simultaneously observe antibody and bacteria due to this problem.

Figure 7:
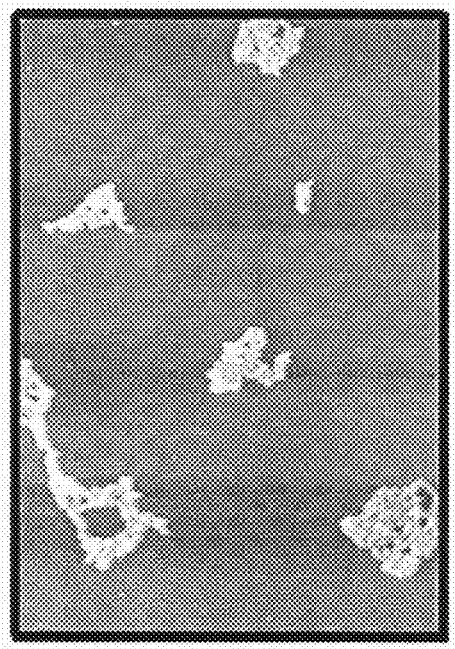
FIG. 7 shows a) large-area (50×30 μm) SPM image of an antibody microarray to RS exposed to the RS bacteria. The overlying grid is used to show the organization of the bacteria aggregates on the array. The antibody pattern is not visible in the image due to the large height of the bacteria. b) Zoom image of one element of the antibody microarray with bound RS bacteria (scan size 16×16 μm). c) Further zoom of aggregated RS bacteria (scan size 3.1×3.1 μm).
Figure 7:
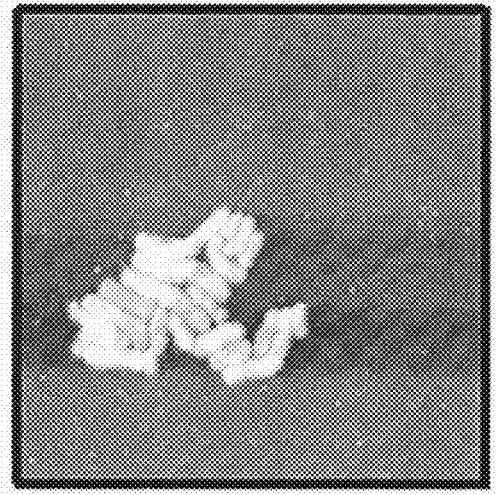
Figure 7:
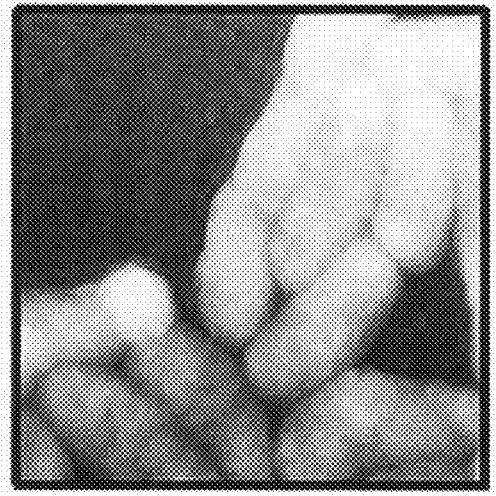

FIG. 7 is a similar non-contact SPM image of patterned antibody to RS after incubation with a solution of RS bacteria at a concentration of $3 \times 10^7$ cell/ml. Depending on bacteria concentration, different amounts of bacteria are bound to the printed antibody surface (see FIG. 6*b* and FIG. 7*a*). Bacteria bound to the RS antibody in FIG. 7 were aggregated at this concentration. A reference grid was added in FIG. 7*a* to help show that the aggregate RS cells form a pattern on the microarray. The centers of the antibody patterns are 15 microns apart as expected from the known geometry of the stamped array. Addition of Tween to the buffer solution prevents non-specific adsorption to the glass substrate and also helps to disperse the cells. At this concentration of bacteria and for an exposure time of 40 minutes, it was estimated that 30% of the microarray surface was coated by the RS bacteria.

Because of the checkerboard pattern of the antibody arrays, it is possible to use optical microscopy to detect the presence of the bacteria. While a positive identification of bacteria on any one square of the pattern might require careful optical microscopy examination, the appearance of a periodic pattern of squares can be quickly detected using ordinary optical microscopy. Digitized images clearly show that at these concentrations, the bacteria confined to antibody regions produce well-defined optical patterns that can be easily detected.

Figure 8:
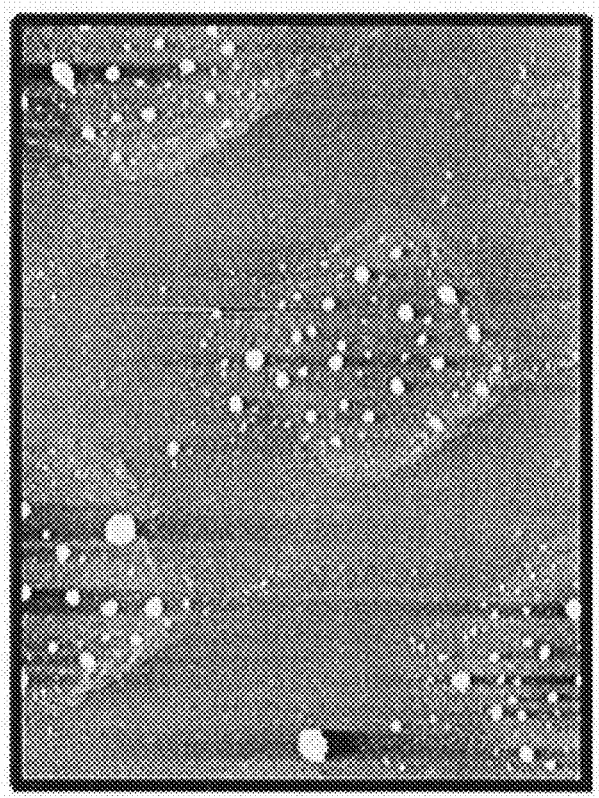
FIG. 8 shows a) SPM image of microarray of E. coli antibody after incubation with E. coli bacteria (scan size 35×25 μm) and b) SPM image of a microarray of RS antibody after incubation with E. coli bacteria (scan size 40×28 μm).
Figure 8:
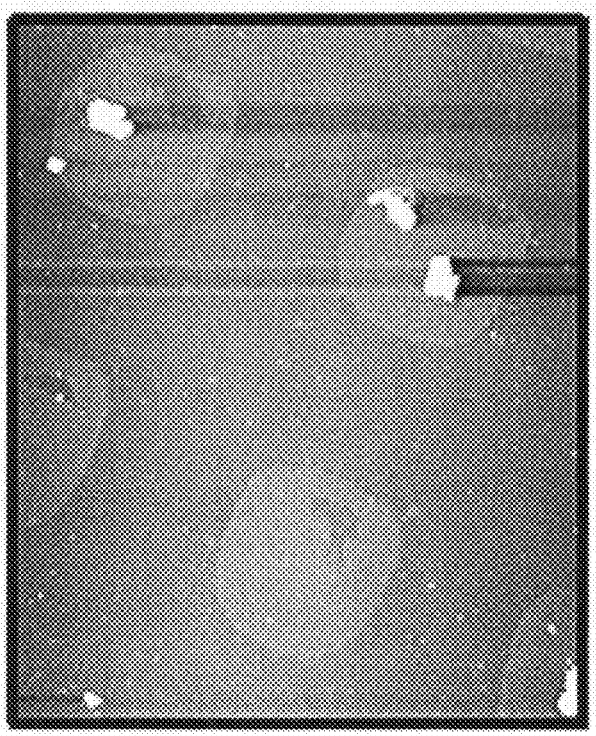

Cross-reaction studies were also conducted to determine the degree to which antibody to RS bacteria will interact with *E. coli* bacteria. FIG. 8*a* shows a printed microarray of *E. coli* antibody after incubation with a solution of *E. coli* (concentration $7 \times 10^7$ cell/ml) for 40 minutes. Incubation times of this duration produced no detectable degradation of the patterned arrays. There is clear evidence for the selective binding of the *E. coli* to its antibody. Similarly, a printed microarray of RS antibody was also exposed to a solution of *E. coli* at a concentration of $7 \times 10^7$ cell/ml for 40 minutes. A comparison between image 5*a* and 5*b* shows a dramatic reduction in the number of bound objects when the RS antibody array was exposed to *E. coli* 0157:H7. Similar experiments also showed that RS bacteria do not exhibit a selective binding to the *E. coli* antibody (data not shown). These initial experiments support the claim that only specific bacteria will bind with complementary antibody. The results also indicate that the bacteria remain immunologically active even after death.

CONCLUSION

We describe a simple technique for fabrication of antibody microarrays capable of detecting bacteria. The microarrays were fabricated by inexpensive μCP methods. The fabrication of the arrays was optimized by careful characterization by scanning probe microscope techniques. SPM studies of exposed antibody arrays indicated a high specificity of bacteria binding to their complementary antibody. The results of the cross-reaction studies show that the bacteria exhibit a low binding selectivity to non-complementary antibodies.

This work demonstrates how microarrays coupled with the high-resolution scanning probe capabilities can be a sensitive tool for bacterial detection, and paves the way for the fabrication of multiple antibody microarrays for the simultaneous detection of a wide variety of bacteria.

Example II

Redundant Protein Patterning Via Microfluidic Networks

Figure 9:
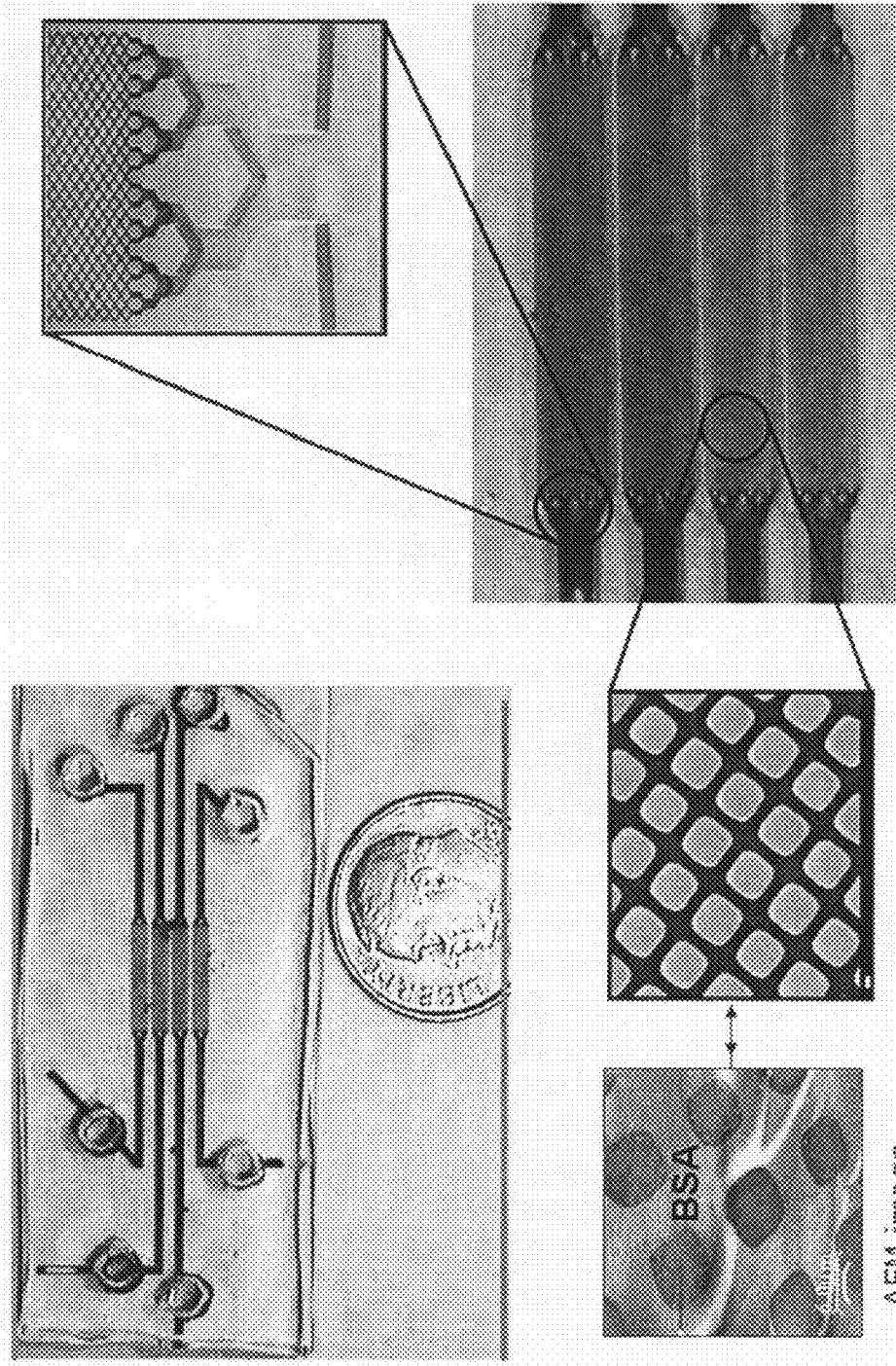
FIG. 9 shows a representative 4-column sensor chip.

We used poly(dimethylsiloxane) (PDMS) in a microfluidic deposition network (MFN) procedure to create redundant multiple protein microarrays in a checkerboard pattern onto functionalized glass surface, thereby creating biologically active surfaces for use as immunosensors. The prototype 4-column sensor chip is shown in FIG. 9. The squares are approximately 10 μm by 10 μm, 10 μm apart, and 10 μm deep. The design of our MFN was optimized for use in a scanning probe microscope (SPM), such that multiple squares in the checkerboard pattern were visible within the maximum scan area in the microscope (about 40 μm by 40 μm). SPM and fluorescence microscopy (FM) were used to characterize the microarrays before and after performing multiple immunoassays. Additional efforts were made to minimize the adsorption of PDMS to the surface by blocking the entire PDMS MFN stamp with bovine serum albumin (BSA).

Figure 10:
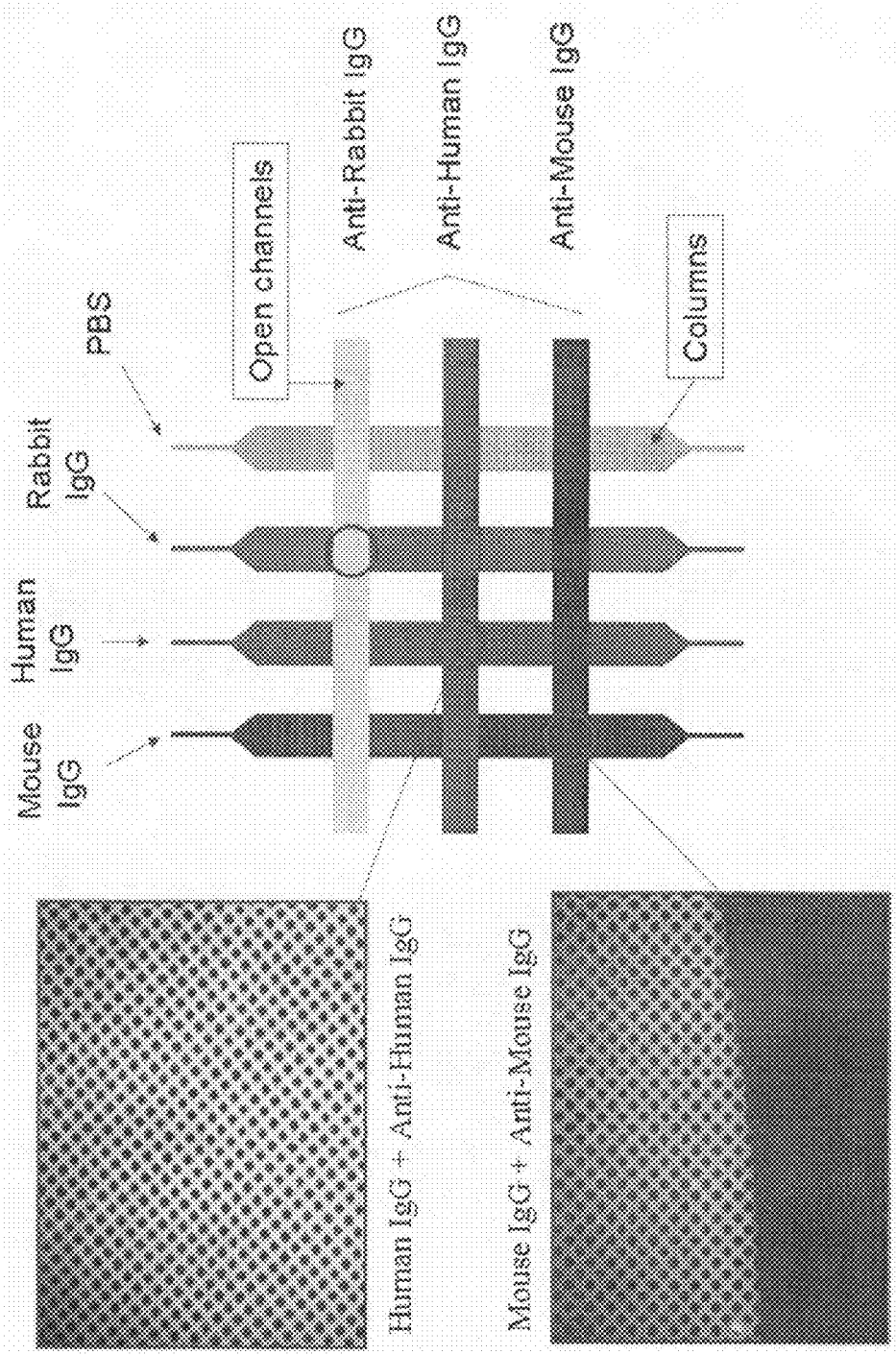
FIG. 10 shows a multi-analyte microfluidic assay platform.
Figure 11:
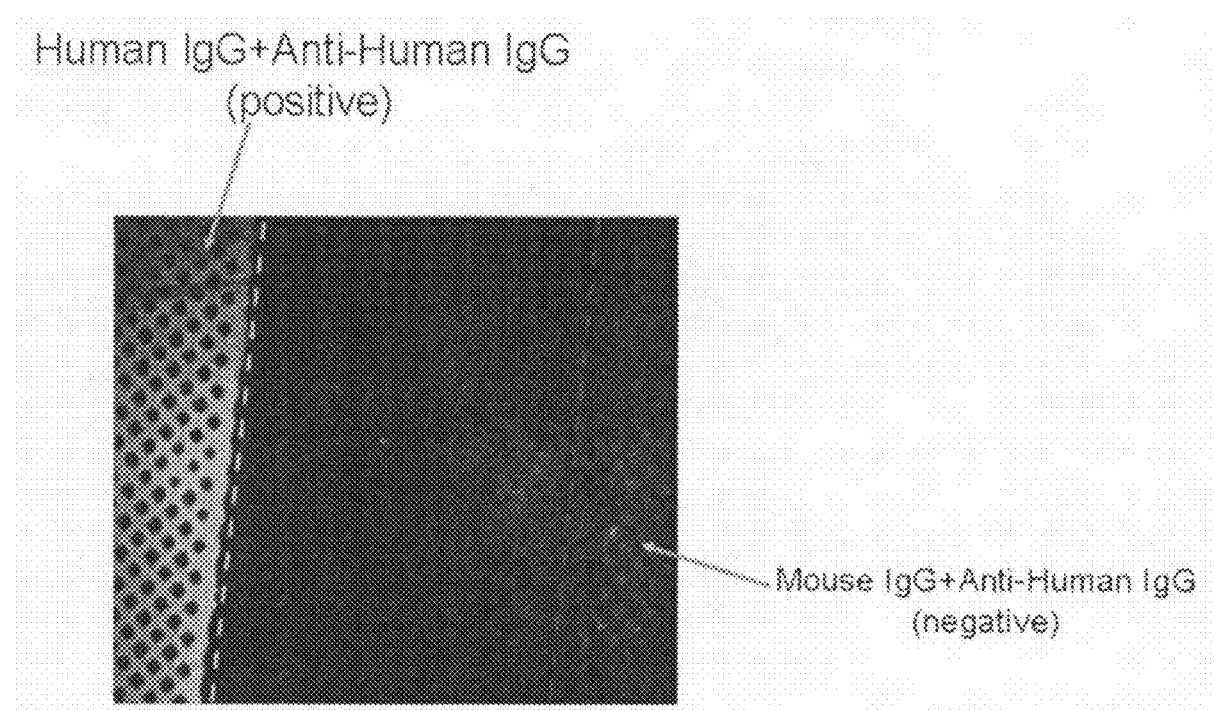
FIG. 11 shows positive and negative binding of an anti-IgG analyte to redundant microarrays of IgG.

Protein microarrays fabricated with the MFN stamp were used in several cross-reaction studies of mouse, human and rabbit immunoglobulin (IgG) proteins to confirm specificity of binding to anti-mouse IgG, anti-human IgG and anti-rabbit IgG, respectively. IgG was deposited using microfluidic techniques. The PDMS chip was then peeled off and the uncovered area was blocked with bovine serum albumin to reduce nonspecific binding. The chip was then incubated with solutions of the various anti-IgG (FIG. 10). Positive results were obtained for complementary IgG/anti-IgG pairs, whereas binding was not observed in the experiments that involved exposure of the to the non-complementary anti-IgG (FIG. 11). This work demonstrates that a PDMS channel stamp can be use to create redundant patterns of sensing proteins, thereby making it possible to detect various pathogens using pattern recognition algorithms.

Example III

Analyte Concentration, Exposure Time and Pattern Analysis

Experiments pertaining to evaluate sensitivity of detection as a function of analyte concentration and exposure time were performed using bacteria, specifically RS, as the analyte. By using bacteria, the assay can be imaged under a dark field microscope and analyzed visually. This avoided a problem associated with fluorescence detection, wherein the pixels on the CCD camera can become overexposed when measuring the intensity of the photons emitted from a fluorescing sample as, for example, when IgG is used as the analyte.

Microarray chips. PDMS stamps contained a patterned array of anti-RS antibody that included functionalized areas of 10 μm by 10 μm square, separated from each other by 5 μm. Both RS bacteria and anti-RS antibody were obtained from Kirkegaard & Perry Laboratories, (Gaithersburg, Md., USA).

Variation in bacterial analyte concentration. Four samples were generated. The first two samples, stamps 1 and 2, were exposed to a 1:1000 dilution of RS positive control, yielding a concentration of $3.09 \times 10^6$ cells/ml. The remaining two stamps, stamps 3 and 4, were exposed to a 1:100 dilution of RS bacteria, giving an exposure concentration of $3.09 \times 10^7$ cells/ml. The exposure time was 40 minutes.

Variation in exposure time. For this experiment, four samples were again generated, and exposed to the same analyte concentration $3.09 \times 10^7$ cells/ml. However, the samples were exposed for different periods of time: 10 minutes, 20 minutes, 30 minutes and 40 minutes.

Figure 12:
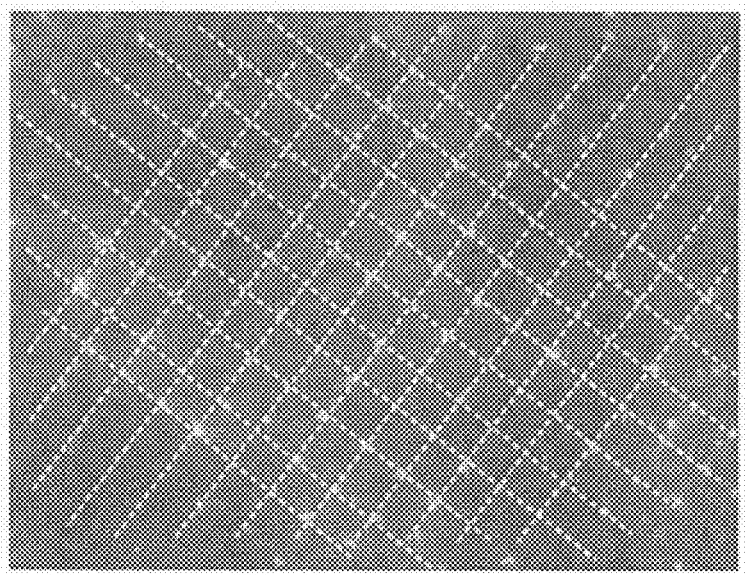
FIG. 12 shows an image of an RS bacterial assay taken with a dark field microscope overlaid with a doted grid. The bacteria appear as white dots in this image and appear to form a periodic pattern.

Detection of analyte binding. The samples were imaged using a Nikon Epiphot 200 dark field microscope. For the concentration experiments, pictures were taken of a total of 13 different areas. For the exposure time experiments, 16 images were taken, four images per each exposure time. A grid-like formation was evident in the images, as shown in FIG. 12. The bacteria appear as white dots in this image.

Figure 13:
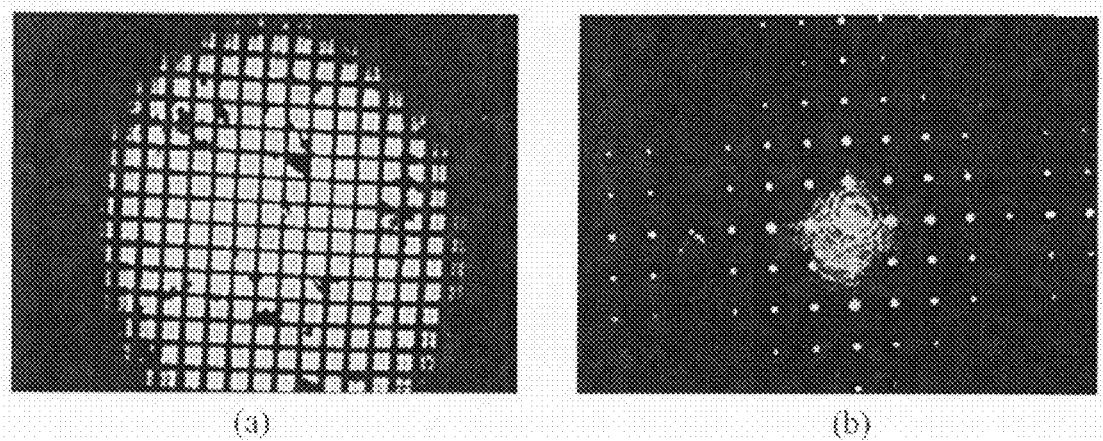
FIG. 13 shows a) an image of a slightly dusty square mesh and b) a Fourier transform of the image a).
Figure 14:
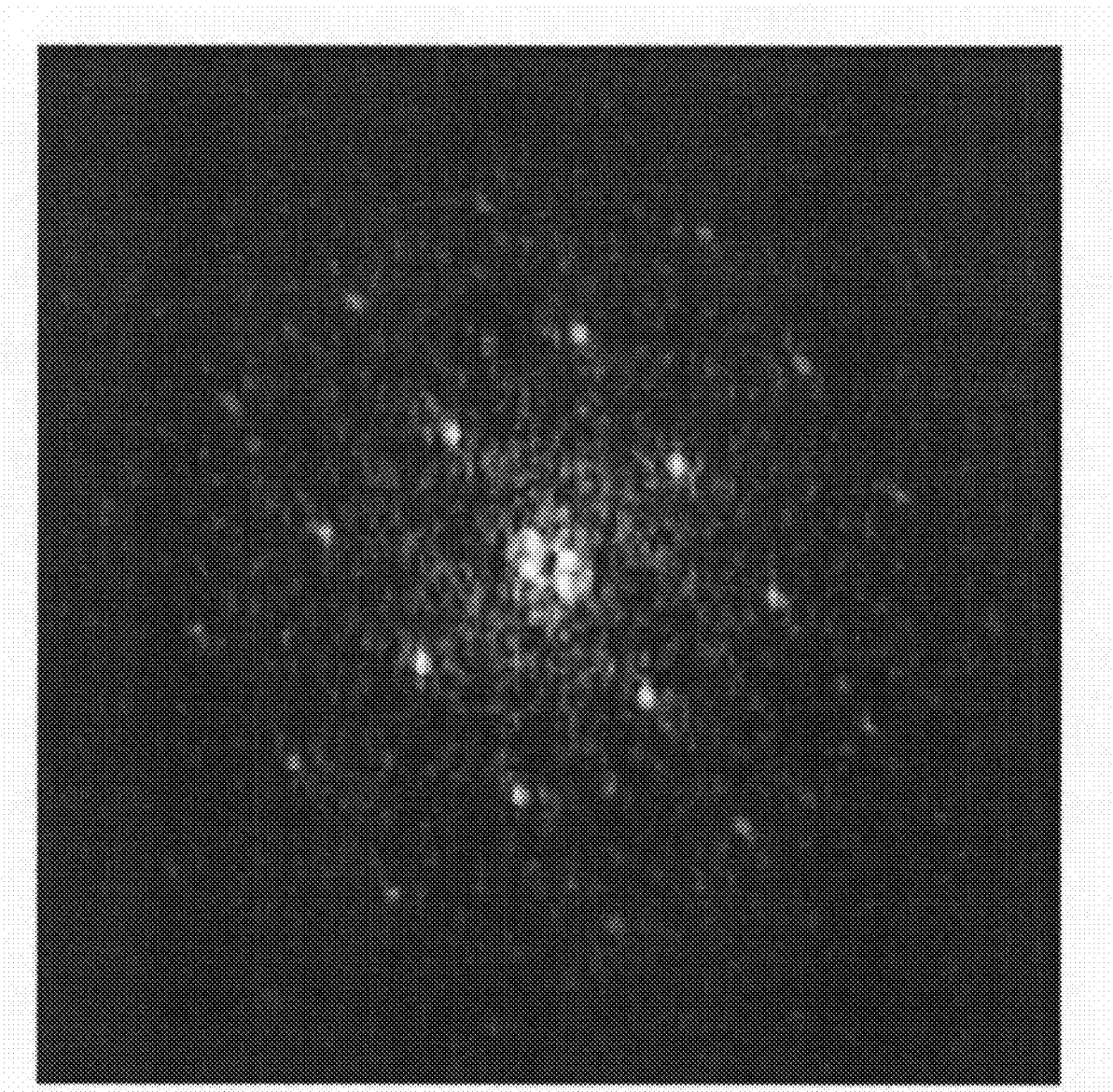
FIG. 14 shows a Fourier transform of the image in FIG. 12.

Pattern analysis. To determine whether or not the images on the microscope were actually periodic, the images were analyzed in Adobe PhotoShop by performing Fourier transformations. If an image has certain periodicity, the Fourier transform will appear in a specific pattern. To illustrate, the analysis software was presented with an image of an object with a known square periodicity. The image and its Fourier transform of the image is shown in FIG. 13. As can be seen in FIG. 14 the Fourier transform of the experimental image for the concentration experiment (FIG. 12) also shows the pattern expected for square periodicity.

Once the Fourier transformation has been performed, it is possible to determine the actual periodicity of the bacteria in the image using Equation (1):

$$p = na/r \tag{1}$$

where p is the number of pixels of periodicity, n is the order number of the transformation, r is the radius of the transformation, and a is the length of one side of the transformation. All of the measurements for Equation (1) are in pixels.

Our microscope was calibrated using a 100 μm aperture. We determined that 11.2 μm was equal to 79 pixels in the image. Calibration makes it is possible to determine the periodicity of the patterned bacteria. All our measurements were initially obtained in the first order of the Fourier transform, thus setting n equal to one in Equation (1). Using Adobe PhotoShop, the values for a and r were measured in pixels.

In the concentration experiments, it was found that the length of one side of our image, a, was 1024 pixels and the radius of the Fourier transform, r, was 10 pixels. By placing these values into Equation (1), the periodicity, p, was determined to be 102 pixels. Converting the periodicity from pixels into microns, it was determined that the periodicity of the patterned bacteria was 14.4 μm. Given that each square on the antibody pattern is 10 μm by 10 μm square, and the square are all separated from each other by 5 μm, the bacteria would have an expected periodicity of approximately 15 μm, if it is assumed that the bacteria are located in the center of each antibody square.

The calibration of the microscope also allows us to analyze the images visually to determine the coverage of a sample or the number of bacteria on a sample and how it corresponds to the exposure concentration of the bacteria. By measuring the calibration marks, it was determined that each bacterium in the pattern would be separated from the next by approximately 15 μm. Thus, a 15 μm by 15 μm grid was created that could be overlaid on the images. In doing so, the number of squares in the grid in which there was at least one bacterium reflected the number of squares on the patterned image that were covered with bacteria, and the number of bacteria per grid square reflected the number of bacteria per patterned square.

On each image, there were 191 squares available from the grid. For each image, the number of squares with bacteria in them were counted, and for each image the number of total bacteria on that section of the sample was totaled in order to account for there being more than one bacterium per square. The results of the counts are exhibited in Table 1. Table 2 shows averages, for each concentration, of the number of squares with bacterial coverage, the number of total bacteria on the image, and the percentage of squares covered.

TABLE 1

Bacterial coverage of samples for differing concentrations of bacteria (191 squares per image)

| Concentration | Image | Number of Squares Covered | Total Number of Bacteria on Image |
|---|---|---|---|
| $3.09 \times 10^6$ cells/ml | 1 | 61 | 68 |
| | 2 | 62 | 86 |
| | 3 | 64 | 80 |
| | 4 | 91 | 117 |
| | 5 | 91 | 114 |
| $3.09 \times 10^7$ cells/ml | 6 | 96 | 129 |
| | 7 | 87 | 125 |
| | 8 | 95 | 129 |
| | 9 | 101 | 117 |
| | 10 | 99 | 122 |
| | 11 | 111 | 143 |
| | 12 | 113 | 156 |
| | 13 | 106 | 146 |

TABLE 2

Averages for each concentration of bacterial analyte

| Concentrations | $3.09 \times 10^6$ cells/ml | $3.09 \times 10^7$ cells/mi |
|---|---|---|
| Avg. Number of Squares Covered | 74 ± 14 | 101 ± 8 |
| Avg. Total Number of Bacterial per Image | 92 ± 21 | 133 ± 12 |
| Percent Coverage | 39% | 53% |

It can be concluded that if the concentration increases by a factor of ten, the percentage of squares covered only increases by 12 percentage points. This implies that the biosensor is not very sensitive for changes at higher concentrations. However, it may be sensitive to changes in low concentrations, as the percent coverage may increase more quickly.

The Fourier analysis in the exposure time experiments also provided evidence of square periodicity, as expected, and the periodicity of the bacteria was found to be 14.5 μm for each of the images. The images were analyzed visually with the same 15 μm by 15 μm grid used for the concentration experiments. On each image the grid covered 191 squares. These squares were then counted, as described above, to determine how many squares per image were covered with bacteria in order to determine the percent coverage of the sample. The number of bacteria per image was also totaled in order to account for multiple bacteria attached to squares. The results are exhibited in Table 3 and the averages are shown in Table 4.

TABLE 3

Bacterial coverage of samples for differing exposure times (191 squares per image)

| Exposure Time | Image | Number of Squares Covered | Total Number of Bacteria |
|---|---|---|---|
| 40 minutes | 1 | 98 | 134 |
| | 2 | 94 | 109 |
| | 3 | 112 | 150 |
| | 4 | 104 | 131 |
| 30 minutes | 5 | 80 | 102 |
| | 6 | 93 | 113 |
| | 7 | 91 | 119 |
| | 8 | 85 | 106 |
| 20 minutes | 9 | 73 | 79 |
| | 10 | 77 | 87 |
| | 11 | 91 | 101 |
| | 12 | 87 | 106 |
| 10 minutes | 13 | 29 | 34 |
| | 14 | 73 | 85 |
| | 15 | 45 | 51 |
| | 16 | 31 | 36 |

TABLE 4

Averages for each of bacterial analyte exposure time

| Stamp | Exposure Time | Avg. Number of Squares | Avg. Total Number of Bacteria | Percent Coverage |
|---|---|---|---|---|
| 1 | 10 min | 44 ± 17 | 51 ± 20 | 23% |
| 2 | 20 min | 82 ± 7 | 93 ± 11 | 43% |
| 3 | 30 min | 87 ± 5 | 110 ± 6 | 46% |
| 4 | 40 min | 102 ± 7 | 131 ± 14 | 53% |

By graphing this date, the exposure times that will result in 100% bacterial coverage of the sample as well as 0% coverage could be estimated.

Example IV

Detection of Analyte Binding Using Capacitance

Impedance, or capacitance calculated from impedance data or measured directly using a capacitance bridge, can be used for detecting binding of an analyte to a sensing molecule. For example, the binding of an antigen (bacteria) to an immobilized antibody can be detected.

A gold electrode surface is covered with insulating layers of a mercaptoacid, such as mercaptohexadecanoic acid or thioctic acid, then reacted with carbodiimide (EDC), which activated immobilization of the antibodies on top of this layer. In this case biorecognition element (IgG) is immobilized covalently to the surface of sensing element. Gold electrodes, commercially available from BAS (West Lafayette, Ind.) were used in a flow cell or electrodes made of gold evaporated on glass were adapted for flow cell.

Figure 15:
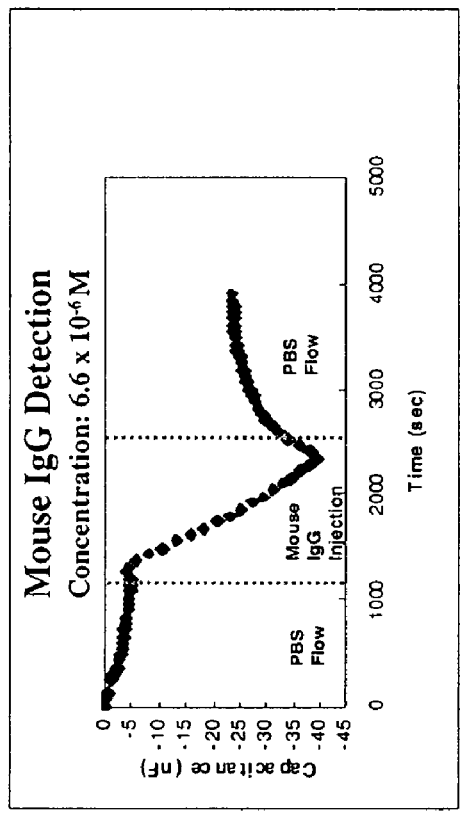
FIG. 15 shows detection of antibody-antigen binding on a gold electrode using impedance detection.

The results are presented in FIG. 15. The difference between signals from electrode with immobilized sensing protein (IgG) and electrode covered with non-binding protein were measured.

Figure 16A:
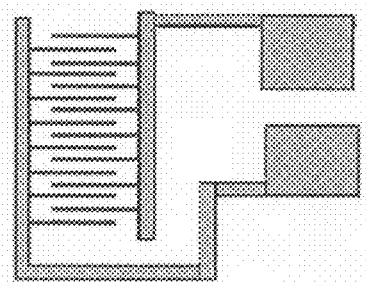
FIG. 16 shows a) a schematic of an interdigitated electrode (IDE), b) optical microscope image of binding of RS bacteria upon exposure of bacteria to IDE functionalized with anti-RS antibody and c) optical image of nonfunctionalized IDE after exposure to RS bacteria.
Figure 16B:
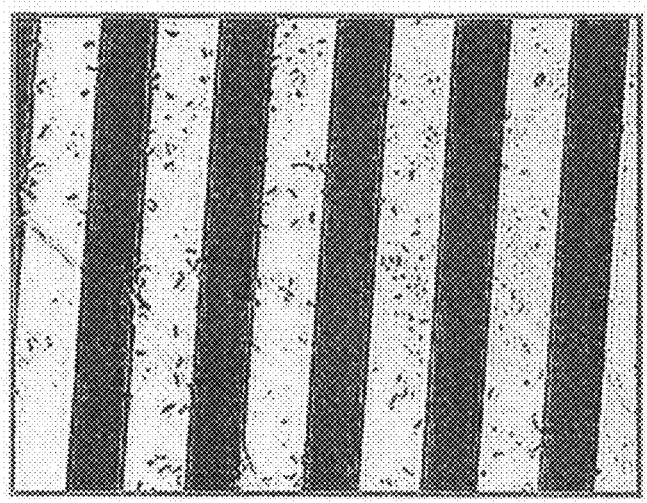
Figure 16C:
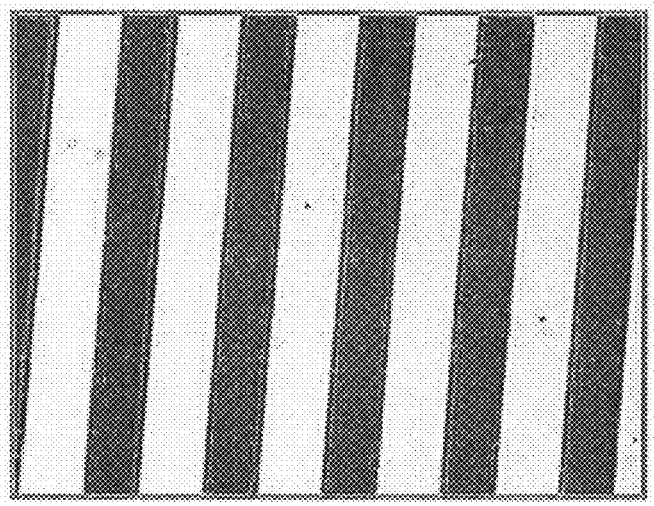

Another approach is to use interdigitated fingers electrodes (FIG. 16a) and capacitance bridge. Those 20 μm wide gold electrodes were covered with antibody to RS bacteria according to method described above and exposed to bacteria (FIG. 16b). The same bare gold electrodes (no antibody immobilized) were exposed to bacteria and no binding was observed (FIG. 16c).

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A method for detecting an analyte comprising:
   providing a substrate surface comprising a microarray comprising multiple positive array elements arranged on the substrate surface in a periodic pattern of array elements, said positive array elements comprising a sensing molecule that targets the analyte;
   flowing a sample comprising the analyte over the substrate surface such that the sample sequentially contacts positive array elements in the microarray under conditions to cause the analyte to interact with the sensing molecules;
   detecting interactions between the analyte and the sensing molecule;
   determining whether the arrangement of the detected interactions on the substrate surface forms a periodic pattern;
   calculating the periodicity of the pattern of detected interactions; and
   comparing the periodicity of the pattern of detected interactions with the periodicity of the pattern of positive array elements, to determine whether the periodicities are essentially the same;
   wherein a determination that the periodicities are essentially the same is indicative of the presence of analyte in the sample.

2. The method of claim 1 wherein the substrate surface is disposed in a channel.

3. The method of claim 2 wherein the sample is introduced into the channel as a point source.

4. The method of claim 1 further comprising analyzing sequentially contacted positive array elements to determine concentration of the analyte in the sample.

5. The method of claim 1 wherein the substrate surface comprises alternating regions in which the microarray is present or absent, such that the sample flow sequentially contacts the alternating regions.

6. The method of claim 5 further comprising analyzing the sequentially contacted microarray regions to determine the concentration of analyte in the sample.

7. The method of claim 5 further comprising analyzing the sequentially contacted microarray regions to determine the level of nonspecific binding of sample components to array elements.

8. The method of claim 1 wherein the microarray further comprises multiple null array elements that do not specifically target the analyte, and wherein the shape of the positive array elements on the substrate surface is different from the shape of the null array elements.

9. The method of claim 1 wherein the pattern periodicity is detected using a computer algorithm.

10. The method of claim 1 wherein the substrate surface comprises a plurality of different microarrays.

11. The method of claim 10 wherein the positive array elements in a first microarray comprise a first sensing molecule, and wherein the positive elements in a second microarray comprise a second sensing molecule.

12. The method of claim 1 wherein the sensing molecule is a biomolecule.

13. The method of claim 12 wherein the biomolecule comprises a protein, glycoprotein, nucleic acid or carbohydrate.

14. The method of claim 1 wherein the analyte is a biomolecule.

15. The method of claim 1 wherein the analyte is a pathogenic organism.

16. A method for detecting an analyte comprising:
   providing a device comprising a channel comprising a surface comprising a microarray comprising positive array elements comprising a sensing molecule that targets the analyte, said positive array elements arranged on the channel surface in a periodic pattern of array elements, said microarray transecting the channel and disposed along a length of the channel;
   flowing a sample comprising the analyte through the channel such that the sample flow sequentially contacts the microarray under conditions to cause the analyte to interact with the sensing molecules;
   detecting interactions between the analyte and the sensing molecule;
   determining whether the arrangement of the detected interactions on the substrate surface forms a periodic pattern;
   calculating the periodicity of the pattern of detected interactions; and
   comparing the periodicity of the pattern of detected interactions with the periodicity of the pattern of positive array elements, to determine whether the periodicities are essentially the same;
   wherein a determination that the periodicities are essentially the same is indicative of the presence of analyte in the sample.

17. The method of claim 16 wherein the sample is introduced into the channel as a point source.

18. The method of claim 16 comprising analyzing sequentially contacted positive array elements to determine concentration of the analyte in the sample.

19. The method of claim 16 wherein the channel comprises a first branch comprising a surface comprising a plurality of microarrays comprising multiple positive array elements comprising a first sensing molecule that targets a first analyte, the positive array elements arranged on the branch surface in a first periodic pattern of array elements; and a second branch comprising a surface comprising a plurality of microarrays comprising multiple positive array elements comprising a second sensing molecule that targets a second analyte, the positive array elements arranged on the branch surface in a second periodic pattern of array elements; and wherein the step of flowing a sample through the channel comprises flowing a sample comprising the first and second analyte through the channel such that the sample flow enters the first and second branches and sequentially contacts the microarray elements under conditions to cause the analyte to interact with the sensing molecules; and wherein the detecting, determining, calculating and comparing steps are performed separately for each branch.

20. The method of claim 19 wherein the concentration of the first analyte in the sample is at least an order of magnitude higher than the concentration of the second analyte, and wherein more of the sample flow is directed to the second branch than the first branch.

21. The method of claim 1 wherein the periodicity is a two-dimensional periodicity.

22. The method of claim 21 wherein the periodicity is a square periodicity.

23. The method of claim 1 wherein the periodicity is a linear periodicity.

24. The method of claim 1 wherein the periodicity cannot be detected without the aid of a computer algorithm.

25. The method of claim 9 wherein the periodicity is detected using a Fourier transform.

* * * * *